(12) United States Patent
Kuroita et al.

(10) Patent No.: US 6,468,998 B1
(45) Date of Patent: Oct. 22, 2002

(54) PYRROLIDINE COMPOUNDS AND MEDICINAL UTILIZATION THEREOF

(75) Inventors: Takanobu Kuroita, Hirakata (JP); Masakazu Fujio, Iruma (JP); Haruto Nakagawa, Fukuoka (JP)

(73) Assignee: Mitsubishi Pharma Corporation, Osaka (JP)

( * ) Notice: Subject to any disclaimer, the term of this patent is extended or adjusted under 35 U.S.C. 154(b) by 0 days.

(21) Appl. No.: 09/830,718

(22) PCT Filed: Oct. 28, 1999

(86) PCT No.: PCT/JP99/06002
§ 371 (c)(1),
(2), (4) Date: May 1, 2001

(87) PCT Pub. No.: WO00/26186
PCT Pub. Date: May 11, 2000

(30) Foreign Application Priority Data

Nov. 2, 1998 (JP) ............................................. 10-311868

(51) Int. Cl.$^7$ .................... C07D 207/14; C07D 403/12; C07D 487/08; A61K 31/40; A61P 9/10
(52) U.S. Cl. .................. 514/214.03; 514/217; 514/220; 514/294; 514/299; 514/304; 514/333; 514/343; 514/411; 514/422; 514/426; 540/581; 540/589; 540/556; 546/94; 546/112; 546/125; 546/256; 546/279.1; 548/441; 548/525; 548/527; 548/528; 548/557
(58) Field of Search .............................. 514/214.03, 217, 514/220, 294, 297, 304, 333, 343, 411, 422, 426; 540/556, 581, 589; 546/94, 112, 12 T, 256, 279.1; 548/441, 525, 527, 528, 557

(56) References Cited

U.S. PATENT DOCUMENTS

| | | | |
|---|---|---|---|
| 3,424,760 A | 1/1969 | Helsley et al. | 260/326.3 |
| 3,424,761 A | 1/1969 | Helsley et al. | 260/326.3 |
| 3,424,762 A | 1/1969 | Helsley et al. | 260/326.3 |
| 3,577,440 A | 5/1971 | Lunsford et al. | 260/326.3 |
| RE29,828 E | 11/1978 | Lunsford et al. | 260/326.47 |
| 4,859,776 A | 8/1989 | Chu et al. | 546/123 |

FOREIGN PATENT DOCUMENTS

| | | |
|---|---|---|
| EP | 0 072 942 | 3/1983 |
| EP | 0 695 545 | 2/1996 |
| EP | 0 813 878 | 12/1997 |
| JP | 49-31985 | 8/1974 |
| JP | 63-13427 | 3/1988 |
| JP | 1-316349 | 12/1989 |
| JP | 3-95157 | 4/1991 |
| JP | 7-506110 | 7/1995 |
| JP | 8-20531 | 1/1996 |
| JP | 10-67684 | 3/1998 |
| WO | 93/22283 | 11/1993 |

OTHER PUBLICATIONS

Grover C. Helsley et al., "Synthesis and biological activity of some 1–substituted 3–pyrrolidinylureas", J. Med. Chem., vol. 11, No. 5, pp. 1304–1037, 1968.

W. Welstead Jr. et al., "Aminoalkylindoles with Central Nervous System Activity", J. Med. Chem., vol. 10, No. 6, pp. 1015–1021, 1967.

G. Helsley et al., "Synthesis and Biological Activity of Some 1–Substituted 3–Pyrrolidinylureas" J. Med. Chem., vol. 11, No. 5, pp. 1034–1037, 1968.

Primary Examiner—Richard L. Raymond
Assistant Examiner—Thomas C McKenzie
(74) Attorney, Agent, or Firm—Wenderoth, Lind & Ponack, L.L.P.

(57) ABSTRACT

The present invention provides a pyrrolidine compound of the formula (I)

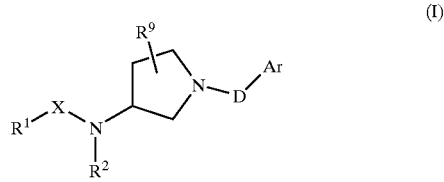

wherein each symbol is as defined in the specification, an optically active compound thereof and a pharmaceutically acceptable salt thereof. The present invention further provides a pharmaceutical composition containing a compound of the formula (I), an optically active compound thereof, or a pharmaceutically acceptable salt thereof, and a pharmaceutically acceptable additive. The compound of the present invention has a serotonin 2 receptor antagonistic action along with a platelet aggregation suppressive action, a peripheral circulation improving action and a lacrimation promoting action. Therefore, the compound of the present invention can be a useful medicine showing effect against thrombotic embolism, dry eye and the like.

12 Claims, No Drawings

PYRROLIDINE COMPOUNDS AND MEDICINAL UTILIZATION THEREOF

This application is a 371 of PCT/JP99/06002 filed Oct. 28, 1999.

TECHNICAL FIELD

The present invention relates to a novel pyrrolidine compound having a potent 5-$HT_2$ receptor antagonistic action and useful as a therapeutic agent for the diseases such as thrombotic embolism, chronic arterial obstruction, intermittent claudication, coronary artery disease, cerebrovascular disorder, peripheral circulatory disturbance, migraine, diabetic peripheral neuropathy, postherpetic neuralgia, glaucoma, dry eye, xerophthalmia, keratitis sicca and the like.

BACKGROUND ART

Serotonin (5-hydroxytryptamine; hereinafter to be referred to as 5-HT) dramatically enhances platelet aggregation due to collagen, epinephrine and adenosine diphosphate (hereinafter to be referred to as ADP). A serotonin 2 (hereinafter to be referred to as 5-$HT_2$) receptor is involved in the promotion of platelet aggregation, erythrocyte deformation, vasoconstriction and blood vessel permeability. Since collateral circulation associated with high 5-HT sensitivity is developed in chronic arterial obstruction, blocking of 5-$HT_2$ receptor should improve the peripheral circulation because it induces vasodilation at the site of lesion rather than systemic one. In view of the above, a 5-$HT_2$ receptor antagonist has been searched and, for example, (3-aminopropoxy)bibenzyl derivative having a platelet aggregation inhibitory activity and usable for the treatment and prevention of thrombosis is disclosed in JP-B-63-13427. In addition, reports have documented that sarpogrelate hydrochloride, which is a selective antagonist to a 5-$HT_2$ receptor, is effective on migraine (J. New Remedies & Clinics, Vol. 45(9), pp. 1833–1836, 1996), on diabetic peripheral neuropathy (Jpn. Pharmacol. Ther., Vol. 24(8), pp. 1853–1857, 1996), and on postherpetic neuralgia (Jpn. Pharmacol. Ther., Vol. 23(7), pp. 1803–1806, 1995). However, the platelet aggregation suppressive action and vasoconstriction suppressive action are not entirely satisfactory and a compound having more superior activity has been demanded.

Moreover, JP-A-8-20531 discloses that 5-$HT_2$ receptor antagonists, inclusive of sarpogrelate hydrochloride, are effective for the treatment of glaucoma and diminished ocular tension, and JP-A-10-67684 discloses that 5-$HT_2$ receptor antagonists, inclusive of sarpogrelate hydrochloride, have a lacrimation promoting action and are effective for the treatment of diseases such as dry eye, xerophthalmia, keratitis sicca and the like.

JP-B-49-31985 discloses a compound having a similar structure to the novel pyrrolidine compound of the present invention. It also discloses a 1-substituted-3-amidopyrrolidine derivative having an analgesic and antidepressant action. Journal of Medicinal Chemistry (J. Med. Chem.), Vol. 10(6), pp. 1015–1021, 1967 discloses an N-substituted-3-amidopyrrolidine derivative as a synthetic intermediate for an aminoalkylindole derivative as a centrally acting drug. Japanese Patent Application under PCT laid-open under Kohyo No. 7-506110 discloses a preparation method of (S)-3-amino-1-substituted-pyrrolidine. JP-A-3-95157 discloses a butenoic acid derivative as a therapeutic agent of coronary artery disease. JP-A-1-316349 discloses a preparation method of (S)-3-aminopyrrolidine and a production method of naphthyridine and quinolonecarboxylic acid having (S)-3-aminopyrrolidine as a side chain. Journal of Medicinal Chemistry (J. Med. Chem.), Vol. 11(5), pp. 1034–1037, 1968, U.S. Pat. Nos. 3,424,760, 3,424,761 and 3,424,762 disclose 3-ureidopyrrolidine derivatives having an analgesic and central action. However, these do not take note of the 5-$HT_2$ receptor antagonistic action or a platelet aggregation inhibitory activity.

DISCLOSURE OF THE INVENTION

The present invention aims at providing a novel compound having a 5-$HT_2$ receptor antagonistic action, a platelet aggregation suppressive action and a peripheral circulation improving action and/or a novel compound having a lacrimation promoting action.

The present inventors have conducted intensive studies and found that a novel pyrrolidine compound of the following formula (I), an optically active compound thereof and a pharmaceutically acceptable salt thereof have a strong 5-$HT_2$ receptor antagonistic action along with a platelet aggregation suppressive action, a peripheral circulation improving action and a lacrimation promoting action. As such, the compound of the present invention can be useful for the treatment of diseases such as thrombotic embolism, chronic arterial obstruction, intermittent claudication, coronary artery disease, cerebrovascular disorder, peripheral circulatory disturbance, migraine, diabetic peripheral neuropathy, postherpetic neuralgia, glaucoma, dry eye, xerophthalmia, keratitis sicca and the like.

Accordingly, the present invention provides the following.

[1] A pyrrolidine compound of the formula (I)

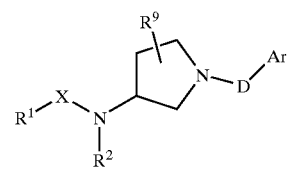

(I)

wherein
$R^1$ is a group selected from the groups of the following formulas (1), (2), (3), (4), (5), (6), (7) and (8)

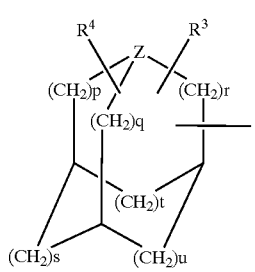

(1)

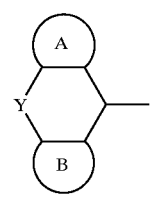

(2)

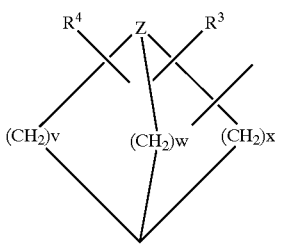

(3)

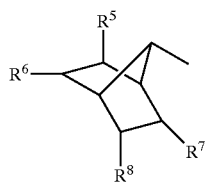

(4)

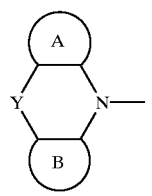

(5)

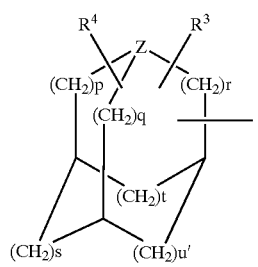

(6)

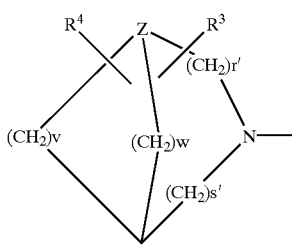

(7)

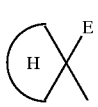

(8)

wherein $R^3$ and $R^4$ are the same or different and each is hydrogen, halogen, alkyl, alkoxy, haloalkyl, hydroxy, amino, dialkylamino, nitro, cyano, amido, or $R^3$ and $R^4$ in combination form carbonyl, $R^5$, $R^6$, $R^7$ and $R^8$ are the same or different and each is hydrogen or alkyl, or $R^5$—$R^6$ and $R^7$—$R^8$ are the same or different and each is bonded to form, together with the bond between the carbon atoms they are bonded to, a double bond, optionally substituted cycloalkyl having 3 to 8 carbon atoms, optionally substituted cycloalkenyl having 3 to 8 carbon atoms, optionally substituted cycloalkadienyl having 5 to 8 carbon atoms, optionally substituted aromatic ring or optionally substituted aromatic heterocycle having, as a heteroatom, at least one atom selected from oxygen atom, nitrogen atom and sulfur atom, ring A and ring B are the same or different and each is optionally substituted cycloalkyl having 3 to 8 carbon atoms, optionally substituted cycloalkenyl having 3 to 8 carbon atoms, optionally substituted cycloalkadienyl having 5 to 8 carbon atoms, optionally substituted aromatic ring or an optionally substituted aromatic heterocycle having at least one atom selected from oxygen atom, nitrogen atom and sulfur atom as a heteroatom, ring H is optionally substituted cycloalkyl having 3 to 8 carbon atoms, E is optionally substituted cycloalkyl having 3 to 8 carbon atoms, Z is carbon atom, nitrogen atom or N-oxide, Y may not be present to make the ring A and ring B independent, or a single bond, oxygen atom, sulfur atom, SO, $SO_2$, $CH_2$, $CH_2CH_2$ or CH=CH, p, q, r, s, t and u are the same or different and each is an integer of 1 or 2, u' is an integer of 0–2, r' and s' are the same or different and each is an integer of 0–3, and v, w and x are the same or different and each is an integer of 1–3, $R^9$ is hydrogen, alkyl having 1 to 6 carbon atoms, alkoxy having 1 to 6 carbon atoms or hydroxyalkyl having 1 to 6 carbon atoms, x is C=O, C=S, NH—C=O, SO or $SO_2$, $R^2$ is hydrogen, alkyl, acyl, optionally substituted arylalkyl, optionally substituted aromatic ring, or an optionally substituted aromatic heterocycle having at least one atom selected from oxygen atom, nitrogen atom and sulfur atom as a heteroatom, D is optionally substituted linear or branched alkylene having 1 to 8 carbon atoms, and when D is branched alkylene, the carbon atom in the branched chain is optionally bonded further to Ar to form 4- to 8-membered ring, and Ar is optionally substituted aromatic ring, optionally substituted aromatic heterocycle or fused aromatic heterocycle having at least one atom selected from oxygen atom, nitrogen atom and sulfur atom as a heteroatom, provided that when X is NH—C=O, SO or $SO_2$, $R^2$ should be hydrogen, alkyl, optionally substituted arylalkyl, optionally substituted aromatic ring or optionally substituted aromatic heterocycle having at least one atom selected from oxygen atom, nitrogen atom and sulfur atom as a heteroatom, when $R^1$ is a group of the formula (5) to formula (7), X should be C=O or C=S and $R^2$ should be hydrogen or alkyl, and when $R^1$ is a group of the formula (5), D should be optionally substituted linear or branched alkylene having 2 to 8 carbon atoms, and when D is branched alkylene, the carbon atom in the branched chain is optionally bonded further to Ar to form 4- to 8-membered ring or an optically active compound thereof or a pharmaceutically acceptable salt thereof.

[2] The pyrrolidine compound of the above-mentioned [1], wherein, in the formula (I), $R^1$ is a group of the formula

[1], (3), (6) or (7), an optically active compound thereof or a pharmaceutically acceptable salt thereof.

[3] The pyrrolidine compound of the above-mentioned [1], wherein, in the formula (I), X is C=O, NH—C=O, SO or $SO_2$, an optically active compound thereof or a pharmaceutically acceptable salt thereof.

[4] The pyrrolidine compound of the above-mentioned [1], wherein, in the formula (I), $R^1$ is a group of the formula (1), X is C=O, $R^2$ is hydrogen, D is ethylene or trimethylene, Ar is optionally substituted aromatic ring or optionally substituted aromatic heterocycle or fused aromatic heterocycle having at least one atom selected from oxygen atom, nitrogen atom and sulfur atom as a heteroatom, $R^3$ and $R^4$ are the same or different and each is hydrogen or alkyl, or $R^3$ and $R^4$ in combination form carbonyl, p, q, r, s, t and u are 1, and Z is carbon atom, an optically active compound thereof or a pharmaceutically acceptable salt thereof.

[5] The pyrrolidine compound of the above-mentioned [1], which is selected from
(S)-N-(1-(2-phenylethyl)pyrrolidin-3-yl)-1-adamantanecarboxamide,
(S)-N-(1-(2-(4-fluorophenyl)ethyl)pyrrolidin-3-yl)-1-adamantanecarboxamide,
(S)-N-(1-(2-(3-fluorophenyl)ethyl)pyrrolidin-3-yl)-1-adamantanecarboxamide,
(S)-N-(1-(2-(2-fluorophenyl)ethyl)pyrrolidin-3-yl)-1-adamantanecarboxamide,
(S)-N-(1-(3-phenylpropyl)pyrrolidin-3-yl )-1-adamantanecarboxamide,
(S)-N-(1-(3-(4-fluorophenyl)propyl)pyrrolidin-3-yl)-1-adamantanecarboxamide,
(S)-N-(1-(2-phenylethyl)pyrrolidin-3-yl) dicyclohexylacetamide,
(S)-N-(1-(2-(4-fluorophenyl)ethyl)pyrrolidin-3-yl) dicyclohexylacetamide,
(S)-N-(1-(2-(4-fluorophenyl)ethyl)pyrrolidin-3-yl)-10,11-dihydrodibenzo[a,d]cycloheptene-5-carboxamide,
(S)-1,1-dicyclohexyl-3-(1-(2-(4-fluorophenyl)ethyl) pyrrolidin-3-yl)urea,
N-methyl-N-(1-(2-(4-fluorophenyl)ethyl)pyrrolidin-3-yl)-1-adamantanecarboxamide, and
(S)-N-(1-(2-(4-fluorophenyl)ethyl)pyrrolidin-3-yl)-(4-azatricyclo[4.3.1.1(3,8)]undecan-4-yl)carboxamide or a pharmaceutically acceptable salt thereof.

[6] A pharmaceutical composition comprising the pyrrolidine compound of the above-mentioned [1], an optically active compound thereof or a pharmaceutically acceptable salt thereof, and a pharmaceutically acceptable additive.

[7] A pharmaceutical agent comprising the pyrrolidine compound of the above-mentioned [1], an optically active compound thereof or a pharmaceutically acceptable salt thereof.

[8] A 5-$HT_2$ receptor antagonist comprising the pyrrolidine compound of the above-mentioned [1], an optically active compound thereof or a pharmaceutically acceptable salt thereof.

[9] A platelet aggregation suppressant comprising the pyrrolidine compound of the above-mentioned [1], an optically active compound thereof or a pharmaceutically acceptable salt thereof.

[10] A lacrimation promoter comprising the pyrrolidine compound of the above-mentioned [1], an optically active compound thereof or a pharmaceutically acceptable salt thereof.

[11] A therapeutic agent for arterial obstruction, antithrombotic drug or peripheral circulation disorder ameliorating agent, which comprises the pyrrolidine compound of the above-mentioned [1], an optically active compound thereof or a pharmaceutically acceptable salt thereof.

In the above-mentioned formula (I), each group is concretely exemplified by the following.

The alkyl at $R^2$ to $R^9$ is linear or branched alkyl having 1 to 18 carbon atoms, such as methyl, ethyl, propyl, isopropyl, butyl, isobutyl, sec-butyl, tert-butyl, pentyl, hexyl, heptyl, octyl, decyl, hexadecyl, octadecyl and the like, with preference given to that having 1 to 6 carbon atoms.

The acyl at $R^2$ is, for example, alkanoyl, arylalkanoyl, aroyl, heteroarylcarbonyl and the like. More specifically, alkanoyl is linear or branched alkanoyl having 1 to 6 carbon atoms, which is, for example, formyl, acetyl, propionyl, butyryl, valeryl, pivaloyl, hexanoyl and the like. The alkanoyl moiety of arylalkanoyl is as mentioned above, which is, for example, benzylcarbonyl, 3-phenylpropionyl, 4-phenylbutyryl and the like. Examples of aroyl include benzoyl, toluoyl, xyloyl, salicyloyl, cinnamoyl, naphthoyl and the like. Examples of heteroarylcarbonyl include furoyl, nicotinoyl, isonicotinoyl, thenoyl and the like, with preference given to acetyl, propionyl, butyryl, benzylcarbonyl, 3-phenylpropionyl, benzoyl, p-toluoyl and the like.

The optionally substituted arylalkyl at $R^2$ consists of alkyl having 1 to 6 carbon atoms and optionally substituted phenyl. Examples thereof include benzyl, 2-phenylethyl, 1-phenylethyl, 3-phenylpropyl, 2-phenylpropyl and the like. Examples of the substituent include (a) halogen such as fluorine, chlorine, bromine, iodine and the like, (b) alkyl having 1 to 6 carbon atoms such as methyl, ethyl, propyl, isopropyl, butyl, isobutyl, tert-butyl and the like, (c) alkoxy having 1 to 6 carbon atoms such as methoxy, ethoxy, propoxy, isopropoxy, butoxy, tert-butoxy and the like, (d) haloalkyl having 1 to,6 carbon atoms such as fluoro-methyl, difluoromethyl, trifluoromethyl and the like, (e) hydroxy, (f) amino, (g) dialkylamino having two same or different alkyl having 1 to 6 carbon atoms, such as dimethylamino, diethylamino, N-methyl-N-ethylamino and the like, (h) nitro, (i) cyano, and (j) amidino optionally substituted by one or more alkyl having 1 to 6 carbon atoms and the like.

The optionally substituted aromatic ring at $R^2$, ring A, ring B, Ar, and $R^5$—$R^6$ and $R^7$—$R^8$, which are respectively bonded together with the bond between the carbon atoms they are bonded to, is, for example, phenyl, naphthyl, 2-indanyl and the like. Examples of the substituent include the aforementioned (a)–(j) and the like.

The optionally substituted aromatic heterocycle having at least one atom selected from oxygen atom, nitrogen atom and sulfur atom as a heteroatom at $R^2$, ring A, ring B, Ar, and $R^5$—$R^6$ and $R^7$—$R^8$, which are respectively bonded together with the bond between the carbon atoms they are bonded to, is, for example, pyridyl, furyl, thienyl, pyrimidinyl and the like. Examples of the substituent include the aforementioned (a)–(j) and the like.

The halogen at $R^3$ and $R^4$ is, for example, fluorine, chlorine, bromine, iodine and the like.

The alkoxy at $R^3$, $R^4$ and $R^9$ is that having 1 to 6 carbon atoms, such as methoxy, ethoxy, propoxy, isopropoxy, butoxy, tert-butoxy and the like.

The haloalkyl at $R^3$ and $R^4$ is that having 1 to 6 carbon atoms, such as fluoromethyl, difluoromethyl, trifluoromethyl and the like.

The dialkylamino at $R^3$ and $R^4$ is that having two same or different alkyl having 1 to 6 carbon atoms, such as dimethylamino, diethylamino, N-methyl-N-ethylamino and the like.

The amido at $R^3$ and $R^4$ is a group consisting of acyl at $R^2$ and amino, such as formamido, acetamido, propanamido, butanamido, cyclohexanecarbonylamino, benzamido, benzylcarbonylamino and the like.

The hydroxyalkyl at $R^9$ is that having 1 to 4 carbon atoms, such as hydroxymethyl, hydroxyethyl, hydroxypropyl, hydroxybutyl and the like.

The optionally substituted cycloalkyl having 3 to 8 carbon atoms at ring A, ring B, ring H, E, and $R^5$—$R^6$ and $R^7$—$R^8$, which are respectively bonded together with the bond between the carbon atoms they are bonded to, is, for example, cyclopropyl, cyclobutyl, cyclopentyl, cyclohexyl, cycloheptyl, cyclooctyl and the like. Examples of the substituent include the aforementioned (a)–(j) and the like.

The optionally substituted cycloalkenyl having 3 to 8 carbon atoms at ring A, ring B, and $R^5$—$R^6$ and $R^7$—$R^8$, which are respectively bonded together with the bond between the carbon atoms they are bonded to, is, for example, that wherein one hydrogen molecule left the above-mentioned cycloalkyl to make one double bond in the ring. Examples thereof include 2-cyclopentenyl, 2-cyclohexenyl, 2-cycloheptenyl, 2-cyclooctenyl and the like. Examples of the substituent include the aforementioned (a)–(j) and the like.

The optionally substituted cycloalkadienyl having 5 to 8 carbon atoms at ring A, ring B, and $R^5$—$R^6$ and $R^7$—$R^8$, which are respectively bonded together with the bond between the carbon atoms they are bonded to, is, for example, that wherein two hydrogen molecules left the above-mentioned cycloalkyl to make two double bonds in the ring, which double bonds being optionally conjugated. Examples thereof include cyclopentadienyl, 1,3-cyclohexadienyl, 1,4-cyclohexadienyl, 1,3-cycloheptadienyl, 1,4-cycloheptadienyl, 1,3-cyclooctadienyl, 1,4-cyclooctadienyl, 1,5-cyclooctadienyl and the like. Examples of the substituent include the aforementioned (a)–(j) and the like.

The optionally substituted fused aromatic heterocycle having at least one atom selected from oxygen atom, nitrogen atom and sulfur atom as a heteroatom at Ar is a fused structure wherein aromatic heterocycle and aromatic ring or aromatic heterocycle share part of each ring. Examples thereof include 1,2-benzisoxazol-3-yl, 1,2-benzisothiazol-3-yl, indol-3-yl, 1-benzofuran-3-yl, 1-benzothiophen-3-yl and the like. Examples of the substituent include the aforementioned (a)–(j) and the like.

The optionally substituted linear or branched alkylene having 1 to 8 carbon atoms at D is, for example, methylene, ethylene, trimethylene, tetramethylene, pentamethylene, hexamethylene, octamethylene, methylmethylene, dimethylmethylene, 1-methylethylene, 2-methylethylene, 1,1-dimethylethylene, 2,2-dimethylethylene, ethylmethylene, diethylmethylene, 1-ethylethylene, 2-ethylethylene, 1-methyltrimethylene, 1,1-dimethyltrimethylene, 2-methyltrimethylene, 2,2-dimethyltrimethylene, 3-methyltrimethylene, 3,3-dimethyltrimethylene, 1-ethyltrimethylene, 2-ethyltrimethylene, 3-ethyltrimethylene and the like. Examples of the substituent include (a) alkoxy having 1 to 6 carbon atoms, such as methoxy, ethoxy, propoxy, isopropoxy, butoxy, tert-butoxy and the like, (b) hydroxy, (c) acyloxy having 2 to 6 carbon atoms, such as acetoxy, propionyloxy, butyryloxy, isobutyryloxy, valeryloxy, isovaleryloxy, pivaloyloxy and the like, (d) —O—$(CH_2)l$—COOH wherein l is an integer of 1–5, such as —O—$(CH_2)_2$—COOH, —O—$(CH_2)_3$—COOH and the like, (e) —O—CO—$(CH_2)m$—COOH wherein m is an integer of 1–3, such as —O—CO—$(CH_2)_2$—COOH, —O—CO—$(CH_2)_3$—COOH and the like, and the like.

When D is branched alkylene, the carbon atom in the branched chain is further bonded to Ar to form a 4- to 8-membered ring. Specifically, when Ar is phenyl, D and Ar in combination form (2,3-dihydroinden-2-yl)methyl, (2,3-dihydroinden-2-yl)ethyl, (2,3-dihydroinden-1-yl)methyl, 2,3-dihydroinden-2-yl, (1,2,3,4-tetrahydro-1-naphthyl)methyl, (1,2,3,4-tetrahydro-2-naphthyl)methyl, (6,7,8,9-tetrahydro-5H-benzocyclohepten-7-yl)methyl and the like. The same applies to the case where Ar is aromatic heterocycle or fused aromatic heterocycle having at least one atom selected from oxygen atom, nitrogen atom and sulfur atom as a heteroatom.

The ring A and ring B are the same or different and each is preferably phenyl, cyclopentyl, cyclohexyl or cycloheptyl.

It is preferable that Y be not present and make ring A and ring B independent, a single bond, $CH_2CH_2$ or CH=CH.

The particularly preferable substituent for the compound of the present invention is exemplified by the following. That is, $R^1$ preferably has the formula (1), the formula (3), the formula (6) or the formula (7), with more preference given to the formula (1).

X is preferably C=O, C=S, NH—C=O, SO or $SO_2$, with particular preference given to C=O.

$R^2$ is preferably hydrogen or alkyl, with more preference given to hydrogen.

D is preferably alkylene having 2 or 3 carbon atoms, which is specifically ethylene or trimethylene. When D is branched alkylene, and the carbon atom in the branched chain is further bonded to Ar to form a 4- to 8-membered ring, D and Ar in combination preferably form (2,3-dihydroinden-2-yl)methyl, (2,3-dihydroinden-2-yl)ethyl, (1,2,3,4-tetrahydro-1-naphthyl)methyl, (1,2,3,4-tetrahydro-2-naphthyl)methyl and (6,7,8,9-tetrahydro-5H-benzocyclohepten-7-yl)methyl.

Ar is preferably phenyl. Examples of the preferable substituent include chlorine atom and fluorine atom, and the number of the substituent is preferably 1 or 2.

Z is preferably carbon atom.

When $R^1$ is expressed by the formula (1), the following formula (9) is preferable

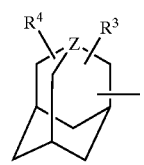

(9)

wherein the following formula (10) is particularly preferable

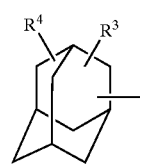

(10)

When $R^1$ is expressed by the formula (3), the following formula (11) is particularly preferable

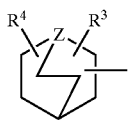

When R¹ is expressed by the formula (6), the following formula (12) or (13) is preferable

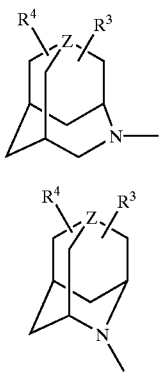

wherein the following formula (14) is particularly preferable

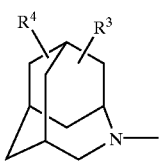

When R¹ is expressed by the formula (7), the following formula (15), (16), (17) or (18) is preferable

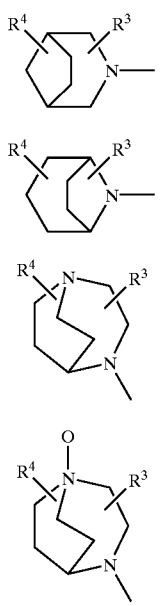

The pharmaceutically acceptable salt of the compound of the formula (I) is exemplified by an acid addition salt with an inorganic acid (hydrochloric acid, hydrobromic acid, sulfuric acid, phosphoric acid, nitric acid and the like) or an organic acid (acetic acid, propionic acid, succinic acid, glycolic acid, lactic acid, malic acid, tartaric acid, citric acid, maleic acid, fumaric acid, methanesulfonic acid, benzenesulfonic acid, p-toluenesulfonic acid, camphorsulfonic acid, ascorbic acid and the like). It is also possible to convert the compound to oxalate for crystallization thereof.

The compound of the formula (I) and a pharmaceutically acceptable salt thereof may be present in the form of a hydrate or a solvate. Thus, hydrates (1/2 hydrate, 1/3 hydrate, 1 hydrate, 3/2 hydrate, 2 hydrate, 3 hydrate and the like) and solvates of these are also encompassed in the present invention. The compound of the formula (I) has at least two kinds of optically active compounds. The optically active compounds thereof are also encompassed in the present invention.

The compound of the present invention encompassed in the formula (I) can be synthesized by, for example, the following method. In the formula, each symbol means the same as defined above, unless particularly indicated otherwise.

1. When R¹ is expressed by the formulas (1)–(4)

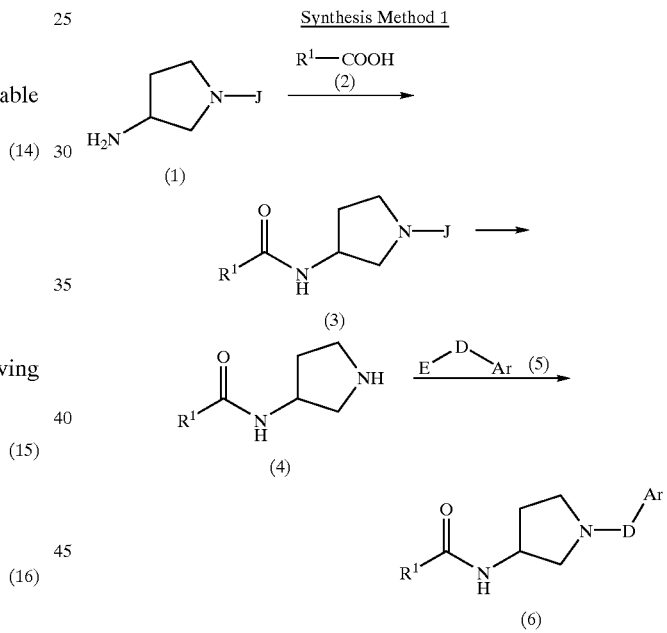

This Synthesis Method is suitable for the synthesis of a compound of the formula (I) wherein X is C=O and R² is hydrogen. A compound of the formula (1) wherein J is amine protecting group (e.g., benzyl, tert-butyloxycarbonyl, benzyloxycarbonyl and the like) generally used in organic synthetic chemistry and a compound of the formula (2) are reacted in a solvent that does not interefere with the progress of the reaction (methylene chloride, chloroform, ethylene dichloride, acetonitrile, tetrahydrofuran (THF), dimethylformamide (DMF), dimethyl sulfoxide (DMSO), or an optionally mixed solvent thereof and the like), in the presence of a base (triethylamine, diisopropylethylamine and the like) generally used in organic synthetic chemistry, from under cooling to refluxing temperature of solvent (preferably 0° C.—room temperature) by adding a condensing agent generally used in organic synthetic chemistry for amine and carboxylic acid (diethyl cyanophosphate, 1,3-dicyclohexylcarbodiimide (DCCD), 1-ethyl-3-(3'- dimethylaminopropyl)carbodiimide (WSCI), benzotriazolyl-N-hydroxytrisdimethylaminophosphonium hexafluorophosphate (Bop reagent) and the like) to give a compound of the formula (3). These reactions generally end in 24 hours.

This compound of the formula (3) can be obtained by once introducing the compound of the formula (2) into carboxylic acid halide, imidazole amide and the like and reacting this compound and a compound of the formula (1) in the presence of a base (triethylamine, diisopropylethylamine and the like) generally used in organic synthetic chemistry, at a temperature of from under cooling to the refluxing temperature of the solvent (preferably 0° C.—room temperature). These reactions generally end in 24 hours.

Furthermore, it can be obtained by reacting a compound of the formula (2) in a solvent that does not interfere with the progress of the reaction (methylene chloride, chloroform, ethylene dichloride, acetonitrile, THF, ethyl acetate, toluene, tert-butyl alcohol, dimethoxyethane, DMF, or an optionally mixed solvent thereof and the like), in the presence of a base (triethylamine, diisopropylethylamine and the like) generally used in organic synthetic chemistry, at a temperature of from under cooling to the refluxing temperature of the solvent (preferably −10° C. to 5° C.), with acid chloride (pivaloyl chloride, ethyloxycarbonyl chloride, isobutyloxycarbonyl chloride (IBCF) and the like) generally used in organic synthetic chemistry to give a mixed acid anhydride, and adding a compound of the formula (1) to allow reaction. These reactions generally end in 24 hours.

Then, the amino protecting group of the compound of the formula (3) is subjected to deprotection under the conditions (4 mol/L hydrochloric acid-dioxane, trifluoroacetic acid, hydrogen-palladium carbon, hydrobromic acid-acetic acid and the like) generally used in organic synthetic chemistry to give a compound of the formula (4). These reactions generally end in 24 hours.

The compound of the formula (4) and a compound of the formula (5), wherein E is a leaving group generally used in organic synthetic chemistry, such as methanesulfonyloxy, p-toluenesulfonyloxy, trifluoromethanesulfonyloxy, chlorine atom, bromine atom, iodine atom and the like, is reacted without solvent or in a solvent that does not interfere with the progress of the reaction (toluene, acetonitrile, THF, DMF, DMSO, water or an optionally mixed solvent thereof and the like) generally used in organic synthetic chemistry, in the presence of a base (triethylamine, diisopropylethylamine, sodium carbonate, sodium hydrogencarbonate, potassium carbonate, sodium hydride, potassium tert-butoxide and the like) generally used in organic synthetic chemistry, at a temperature of from under cooling to the refluxing temperature of the solvent to give the objective compound, the compound of the formula (6). These reactions generally end in 24 hours.

The hydrogen at $R^2$ can be converted to various substituents by reaction generally used in organic synthetic chemistry.

Synthesis Method 2

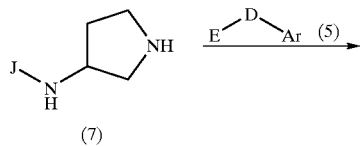

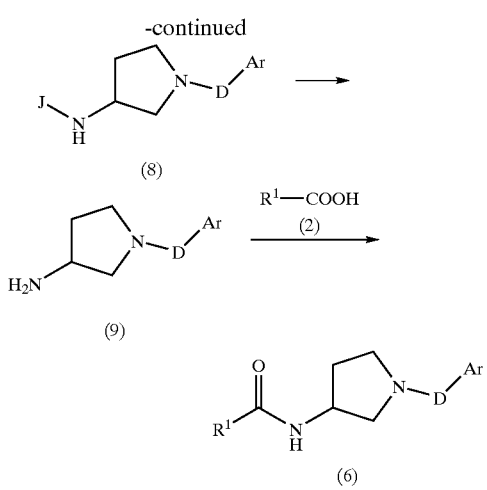

The compound of the formula (6) can be also synthesized by the following method.

A compound of the formula (7) and a compound of the formula (5) are reacted for alkylation of amine as in Synthesis Method 1 to give a compound of the formula (8).

The amino protecting group of this compound is subjected to deprotection according to the deprotection method as in Synthesis Method 1 to give a compound of the formula (9).

The compound of the formula (9) and the compound of the formula (2) are reacted according to a condensation method of carboxylic acid and amine as in Synthesis Method 1 to give the objective compound, the compound of the formula (6).

Synthesis Method 3

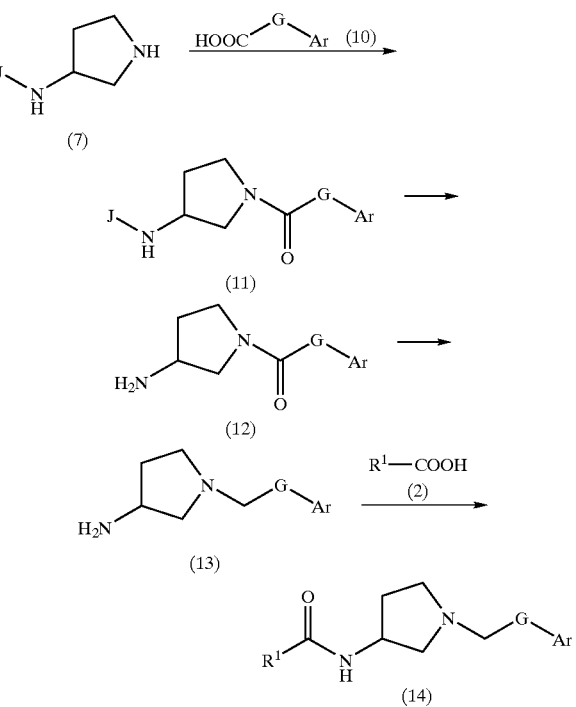

This Synthesis Method is suitable for the synthesis of a compound wherein, in the formula (I), D has 2 or more carbon atoms.

A compound of the formula (7) and a compound of the formula (10), wherein G is linear or branched alkylene having 1 to 7 carbon atoms, are reacted according to a condensation method of carboxylic acid and amine as in Synthesis Method 1 to give a compound of the formula (11).

By deprotection of the amino protecting group of the compound of the formula (11) by a deprotection method as in Synthesis Method 1, a compound of the formula (12) is obtained.

A compound of the formula (12) is reacted in a solvent that does not interfere with the progress of the reaction (diethyl ether, diisopropyl ether, 1,4-dioxane, THF and the like) generally used in organic synthetic chemistry, with a reducing agent (lithium aluminum hydride, diisobutylaluminum hydride, borane ($BH_3$) and the like) generally used in organic synthetic chemistry at −78° C. to the refluxing temperature of the solvent to give a compound of the formula (13). These reactions generally end in 24 hours.

The compound of the formula (13) and the compound of the formula (2) are reacted according to the condensation method of carboxylic acid and amine as in Synthesis Method 1 to give the objective compound, the compound of the formula (14).

Synthesis Method 4

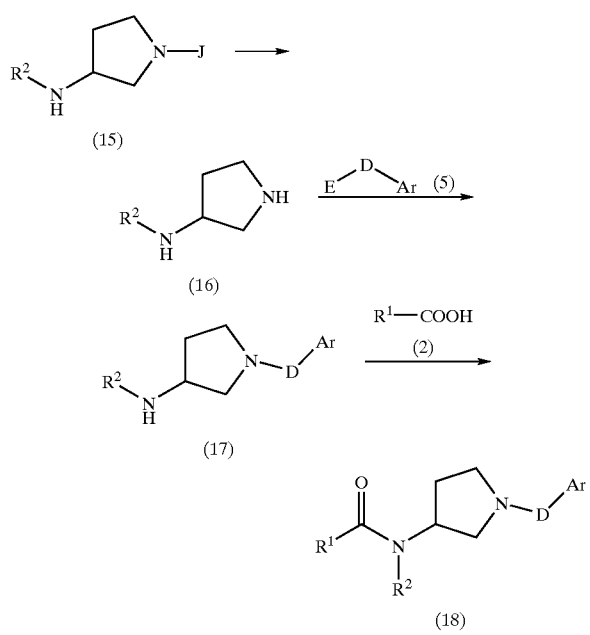

This Synthesis Method is suitable for the synthesis of a compound wherein, in the formula (I), X is C=O and $R^2$ is not hydrogen. The amino protecting group of a compound of the formula (15) obtained according to the method described in Journal of Medicinal Chemistry (J. Med. Chem.), Vol. 10, p. 1015 (1967) is deprotected according to the deprotection method as in Synthesis Method 1 to give a compound of the formula (16).

The compound of the formula (16) and the compound of the formula (5) are reacted for alkylation of amine as in Synthesis Method 1 to give a compound of the formula (17).

The compound of the formula (17) and the compound of the formula (2) are reacted according to the condensation method of carboxylic acid and amine as in Synthesis Method 1 to give the objective compound, a compound of the formula (18).

Synthesis Method 5

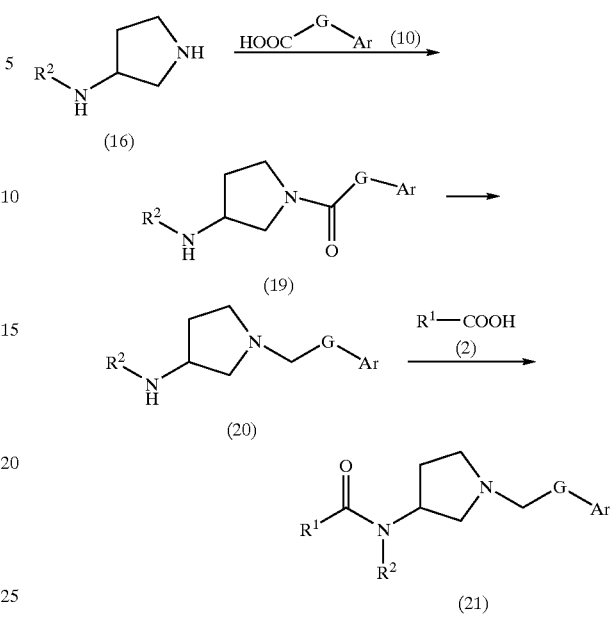

This Synthesis Method is suitable for the synthesis of a compound of the formula (I) wherein D has two or more carbon atoms.

The compound of the formula (16) and the compound of the formula (10) are reacted according to the condensation method for carboxylic acid and amine as in Synthesis Method 1 to give a compound of the formula (19).

The compound of the formula (19) is reduced according to the reduction method of amide as in Synthesis Method 3 to give a compound of the formula (20).

The compound of the formula (20) and the compound of the formula (2) are reacted according to the condensation method for carboxylic acid and amine as in Synthesis Method 1 to give a compound of the formula (21).

Synthesis Method 6

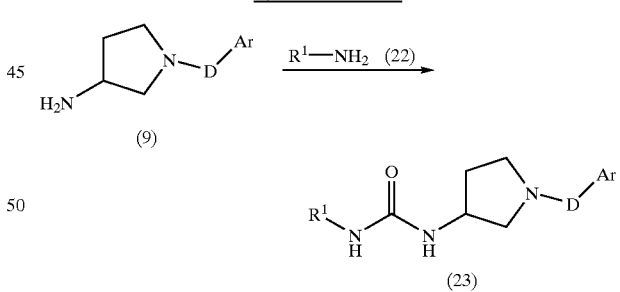

This Synthesis Method is suitable for the synthesis of a compound wherein, in the formula (I), X is NH—C=O and $R^2$ is hydrogen.

A compound of the formula (22) is dissolved in a solvent that does not interfere with the progress of the reaction (THF, toluene and the like) and 1,1'-carbonylbis-1H-imidazole (CDI) is added. The mixture is reacted at a temperature of from under cooling to the refluxing temperature of the solvent (preferably 0° C.—room temperature) and the compound of the formula (9) is added. The mixture is reacted at a temperature of from under cooling to the refluxing temperature of the solvent to give the objective compound, a compound of the formula (23).

The compound of the formula (23) can be also obtained by converting one of a compound of the formula (22) and a compound of the formula (9) according to the method generally used in organic synthetic chemistry to isocyanate and reacting the isocyanate with the other compound.

Synthesis Method 7

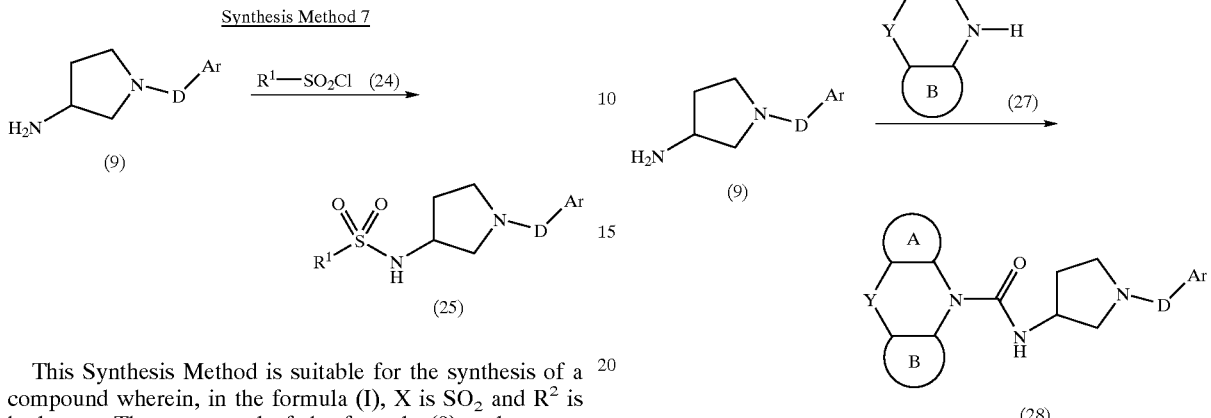

This Synthesis Method is suitable for the synthesis of a compound wherein, in the formula (I), X is $SO_2$ and $R^2$ is hydrogen. The compound of the formula (9) and a compound of the formula (24) are reacted in a solvent that does not interfere with the progress of the reaction (methylene chloride, chloroform, ethylene dichloride, acetonitrile, tetrahydrofuran (THF), dimethylformamide (DMF) or an optionally mixed solvent thereof and the like), in the presence of a base (triethylamine, diisopropylethylamine and the like) generally used in organic synthetic chemistry, at a temperature of from under cooling to the refluxing temperature of the solvent (preferably 0° C.—room temperature) to give the objective compound, a compound of the formula (25).

Synthesis Method 8

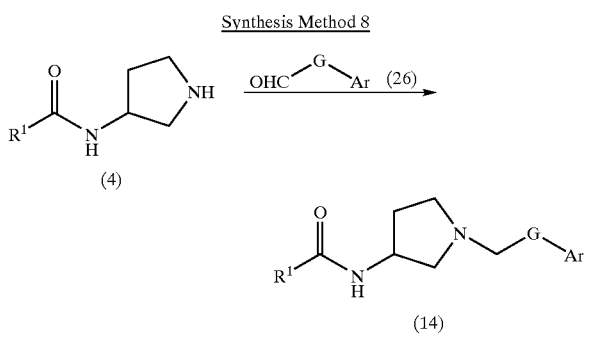

The compound of the formula (14) can be also synthesized by the following method. The compound of the formula (4) and a compound of the formula (26) are reacted in a solvent that does not interfere with the progress of the reaction (methanol, ethanol, propanol, isopropanol, butanol, methylene chloride, chloroform, ethylene dichloride, acetonitrile, tetrahydrofuran (THF), dimethylformamide (DMF), or an optionally mixed solvent thereof and the like), at a temperature of from under cooling to the refluxing temperature of the solvent (preferably 0° C.—room temperature) for 0.1–24 hr. To the reaction mixture is added a reducing agent (sodium borohydride, sodium cyanoborohydride and the like) generally used in organic synthetic chemistry, at a temperature of from under cooling to the refluxing temperature of the solvent (preferably 0° C.—room temperature), and the mixture is reacted at a temperature of from under cooling to the refluxing temperature of the solvent to give the objective compound, a compound of the formula (14).

2. When $R^1$ is expressed by the formulas (5)–(7).

Synthesis Method 9

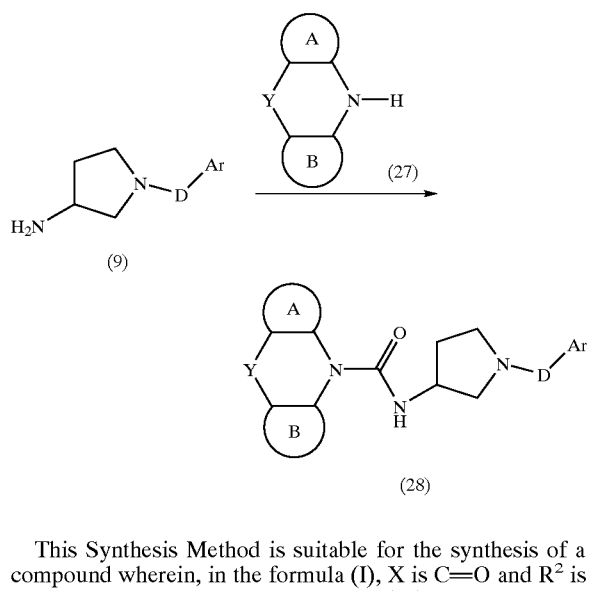

This Synthesis Method is suitable for the synthesis of a compound wherein, in the formula (I), X is C=O and $R^2$ is hydrogen. A compound of the formula (27) is dissolved in a solvent that does not interfere with the progress of the reaction (THF, toluene and the like) and 1,1'-carbonylbis-1H-imidazole (CDI) is added. The mixture is reacted at a temperature of from under cooling to the refluxing temperature of the solvent (preferably 0° C.—room temperature) and a compound of the formula (9) is added. The mixture is reacted at a temperature of from under cooling to the refluxing temperature of the solvent to give a compound of the formula (28).

The compound of the formula (28) can be also obtained by converting the compound of the formula (9) to isocyanate by a method generally used in organic synthetic chemistry and then reacting the isocyanate with the compound of the formula (27).

The hydrogen at $R^2$ can be converted to various substituents by a reaction generally used in organic synthetic chemistry. The amine compound inclusive of the compound of the formula (1), and a carboxylic acid compound inclusive of the compound of the formula (2) and the like, which are synthetic starting materials, are known compounds or can be derived easily from known compounds by the reaction generally used in organic synthetic chemistry.

The compound of the present invention thus obtained can be isolated and purified by a conventional method such as recrystallization, column chromatography and the like. When the obtained product is a racemate, it can be resolved into desired optically active compounds by, for example, fractional recrystallization using an optically active acid or passing the racemate through a column packed with an optically active carrier. Each diastereomer can be separated by fractional crystallization, chromatography and the like. In addition, an optically active compound can be also obtained by the use of an optically active starting material compound and the like. The stereoisomer can be separated by recrystallization, column chromatography and the like.

When a pyrrolidine compound of the present invention, an optically active compound thereof and a pharmaceutically acceptable salt thereof are used as medicines, these are mixed with a carrier acceptable for the preparation of formulations (excipient, binder, disintegrant, flavor, corrective, emulsifier, diluent, solubilizer and the like) to give a pharmaceutical composition or a pharmaceutical preparation (tablet, pill, capsule, granule, powder, syrup, emulsion, elixir, suspension, solution, injection, transfusion, suppository and the like), which can be administered orally or parenterally. A pharmaceutical composition can be prepared into a formulation by a general method. As used in this specification, "parenterally" includes subcutaneous injection, intravenous injection, intramuscular injection, intraperitoneal injection, transfusion and the like.

A preparation for injection, such as an aqueous suspension or oily suspension for sterile injection, can be prepared using a suitable suspending agent or a wetting agent and a suspending agent according to a method known in this field. The preparation for sterile injection may be a sterile injectable solution or suspension using, for example, a non-toxic diluent or solvent that can be administered parenterally, such as an aqueous solution and the like. Examples of usable vehicle and acceptable solvent include water, Ringer's solution, isotonic saline and the like. Furthermore, a sterile non-volatile oil can be generally used as a solvent or a suspending solvent. Any non-volatile oil or fatty acid can be used for this end, which includes natural or synthetic or semi-synthetic fatty oil or fatty acid, and natural or synthetic or semi-synthetic mono- or di- or triglycerides.

The suppository for rectal administration can be produced by mixing a drug with a suitable non-irritative excipient, such as cacao butter, polyethylene glycols and the like, which are solid at ordinary temperature but liquid at a rectal temperature and which dissolves in the rectum to release the drug.

The dosage form of a solid for oral administration is powder, granule, tablet, pill, capsule and the like as mentioned above. In such dosage forms, an active ingredient compound can be mixed with at least one additive, such as sucrose, lactose, cellulose sugar, mannitol, maltitol, dextran, starches, agar, alginates, chitins, chitosans, pectins, gum tragacanth, gum arabic, gelatins, collagens, casein, albumin, synthetic or semi-synthetic polymers or glycerides and the like. The preparations in these dosage forms can contain a further additive as usual, such as inert diluents, lubricants (e.g., magnesium stearate and the like), preservatives (e.g., p-hydroxybenzoates, sorbates and the like), antioxidants (e.g., ascorbic acid, α-tocopherol, cysteine and the like), disintegrants, binders, thickeners, buffering agents, sweeteners, flavors, perfumes and the like. Tablets and pills are produced by further applying an enteric coating. A liquid for oral administration may be pharmaceutically acceptable emulsions, syrups, elixirs, suspensions, solutions and the like, which may contain an inert diluent generally used in this field, such as water.

The pyrrolidine compound of the present invention, an optically active compound thereof and a pharmaceutically acceptable salt thereof have a strong 5-HT$_2$ receptor antagonistic action, and simultaneously show a platelet aggregation suppressive action, a peripheral circulation improving action, and a lacrimation promoting action. Thus, the compound of the present invention is effective as a therapeutic agent for the diseases such as thrombotic embolism, chronic arterial obstruction, intermittent claudication, coronary artery disease, cerebrovascular disorder, peripheral circulatory disturbance, migraine, diabetic peripheral neuropathy, postherpetic neuralgia, glaucoma, dry eye, xerophthalmia, keratitis sicca and the like.

The administration dose is determined depending on age, body weight, general health conditions, sex, diet, administration time, administration method, clearance rate, combination of drugs, severity of the disease for which the patient is undergoing treatments, and other factors. The compound of the present invention, an optically active compound thereof and a pharmaceutically acceptable salt thereof are low-toxic and can be used safely. The daily dose varies depending on the disease state and body weight of the patient, the kind of the compound, administration route and the like. For example, it is desirably about 0.01–50 mg/patient/day, preferably 0.01–20 mg/patient/day, for parenteral administration by subcutaneous, intravenous, intramuscular or rectal administration, and about 0.01–150 mg/patient/day, preferably 0.1–100 mg/patient/day, for oral administration.

EXAMPLES

The present invention is explained in more detail in the following by referring to Starting Material Synthetic Examples, Examples, Formulation Examples and Experimental Examples, which do not limit the present invention in any way.

Starting Material Synthetic Example 1

(S)-N-(1-Benzylpyrrolidin-3-yl)-1-adamantanecarboxamide (10.5 g, described in Example 13) was dissolved in ethanol (100 ml), and 10% palladium-carbon (5 g) was added thereto. The mixture was stirred at room temperature, and to the reaction mixture was added hydrazine monohydrate (1.5 ml). The mixture was stirred under heating for 1 hour. The reaction mixture was cooled to room temperature, and 10% palladium-carbon was filtered off with celite. The filtrate was concentrated, and IPE (isopropyl ether) was added to the obtained residue. The precipitated crystals were collected by filtration to give (S)-N-(pyrrolidin-3-yl)-1-adamantanecarboxamide (7.2 g), melting point 186–188° C.

Starting Material Synthetic Example 2

(S)-3-tert-Butyloxycarbonylamidopyrrolidine (3.0 g) and 2-bromoethylbenzene (3.3 g) were dissolved in DMF (60 ml), and potassium carbonate (6.7 g) was added thereto. The mixture was stirred under heating at 60° C. for 3 hours. After the completion of the reaction, the solvent was evaporated under reduced pressure. The obtained residue was dissolved in chloroform, washed with an aqueous potassium carbonate solution, and dried over magnesium sulfate. The solvent was evaporated under reduced pressure, and the obtained residue was subjected to silica gel column chromatography (chloroform:methanol=40:1). The obtained eluate was concentrated to give (S)-3-tert-butyloxycarbonylamido-1-(2-phenylethyl)pyrrolidine (4.4 g).

(S)-3-tert-Butyloxycarbonylamido-1-(2-phenylethyl) pyrrolidine (4.4 g) was dissolved in trifluoroacetic acid (10 ml) under ice-cooling and the mixture was stirred at room temperature for 1 hour. After the completion of the reaction, chloroform was added. The mixture was adjusted to alkaline with an aqueous potassium carbonate solution, and the mixture was extracted twice with chloroform, and dried over magnesium sulfate. The solvent was evaporated under reduced pressure to give (S)-3-amino-1-(2-phenylethyl) pyrrolidine (2.3 g).

$^1$H-NMR(CDCl$_3$) δ: 1.62–1.76(1H,m), 2.13–2.84(10H, m), 3.44–3.53(1H,m), 7.12–7.30(5H,m)

Starting Material Synthetic Example 3

(S)-3-tert-Butyloxycarbonylamidopyrrolidine (5.0 g) and 2-(4-fluorophenyl)ethyl p-toluenesulfonate (9.5 g) were dissolved in DMF (100 ml). Potassium carbonate (10 g) was added thereto and the mixture was stirred under heating at 60° C. for 3 hours. After the completion of the reaction, the solvent was evaporated under reduced pressure. The obtained residue was dissolved in chloroform, washed with an aqueous potassium carbonate solution, and dried over magnesium sulfate. The solvent was evaporated under reduced pressure, and the obtained residue was subjected to silica gel column chromatography (chloroform:methanol= 40:1). The obtained eluate was concentrated to give (S)-3-tert-butyloxycarbonylamido-1-(2-(4-fluorophenyl)ethyl) pyrrolidine (8.0 g).

(S)-3-tert-Butyloxycarbonylamido-1-(2-(4-fluorophenyl) ethyl)pyrrolidine (8.0 g) was dissolved in trifluoroacetic acid (50 ml) under ice-cooling and the mixture was stirred at room temperature for 1 hour. After the completion of the reaction, chloroform was added. The mixture was adjusted to alkaline with an aqueous potassium carbonate solution, extracted twice with chloroform, and dried over magnesium sulfate. The solvent was evaporated under reduced pressure to give (S)-3-amino-1-(2-(4-fluorophenyl)ethyl)pyrrolidine (5.5 g).

$^1$H-NMR(CDCl$_3$) δ:1.62–1.76(1H,m), 2.15–2.83(10H, m), 3.45–3.56(1H,m), 6.90–7.04(2H,m), 7.12–7.23(2H,m)

Starting Material Synthetic Example 4

1-Benzyl-3-(p-toluenesulfonyloxy)pyrrolidine (3.3 g) and aniline (1.3 g) were mixed and stirred under heating at 160° C. for 3 hours. After the completion of the reaction, the mixture was cooled to room temperature, and an aqueous potassium carbonate solution was added thereto. The obtained mixture was extracted with chloroform, and dried over magnesium sulfate. The solvent was evaporated under reduced pressure, and the obtained residue was subjected to silica gel column chromatography (chloroform:methanol= 40:1). The obtained eluate was concentrated to give 3-anilino-1-benzylpyrrolidine (1.2 g).

3-Anilino-1-benzylpyrrolidine (1.2 g) was dissolved in ethanol (20 ml), 10% palladium-carbon (0.5 g) was added thereto. The mixture was stirred at room temperature, and hydrazine monohydrate (0.24 g) was added. The mixture was stirred under heating for 2 hours and cooled to room temperature. 10% Palladium-carbon was filtered off with celite, and the filtrate was concentrated to give 3-anilinopyrrolidine (0.67 g).

3-Anilinopyrrolidine (0.67 g) and 2-(4-fluorophenyl)ethyl p-toluenesulfonate (1.2 g) were dissolved in acetonitrile (20 ml), and potassium carbonate (2 g) was added. The mixture was refluxed for 3 hours, and after the completion of the reaction, the solvent was evaporated under reduced pressure. The obtained residue was dissolved in ethyl acetate, washed with an aqueous potassium carbonate solution, and dried over magnesium sulfate. The solvent was evaporated under reduced pressure, and the obtained residue was subjected to silica gel column chromatography (chloroform:methanol= 20:1). The obtained eluate was concentrated to give 3-anilino-1-(2-(4-fluorophenyl)ethyl)pyrrolidine (0.83 g).

$^1$H-NMR(CDCl$_3$) δ:1.62–1.76(1H,m), 2.24–2.91(9H,m), 3.80–4.06(2H,m), 6.58(2H,d,J=6 Hz), 6.70(1H,t,J=7 Hz), 6.90–7.04(2H,m), 7.10–7.22(4H,m)

Starting Material Synthetic Example 5

3-Anilinopyrrolidine and 2-bromoethylbenzene are reacted under the same conditions as in Starting Material Synthetic Example 4 to give 3-anilino-1-(2-phenylethyl) pyrrolidine.

Starting Material Synthetic Example 6

3-Methylaminopyrrolidine and 2-bromoethylbenzene are reacted under the same conditions as in Starting Material Synthetic Example 4 to give 3-methylamino-1-(2-phenylethyl)pyrrolidine.

Starting Material Synthetic Example 7

3-Methylaminopyrrolidine and 2-(4-fluorophenyl)ethyl p-toluenesulfonate are reacted under the same conditions as in Starting Material Synthetic Example 4 to give 3-methylamino-1-(2-(4-fluorophenyl)ethyl)pyrrolidine.

Starting Material Synthetic Example 8

(R)-N-(1-Benzylpyrrolidin-3-yl)-1-adamantanecarboxamide (5 g) is reacted under the same conditions as in Starting Material Synthetic Example 1 to give (R)-N-(pyrrolidin-3-yl)-1-adamantanecarboxamide (3.5 g), melting point 187–189° C.

The formulas of the compounds obtained in the above-mentioned Starting Material Synthetic Examples are as follows.

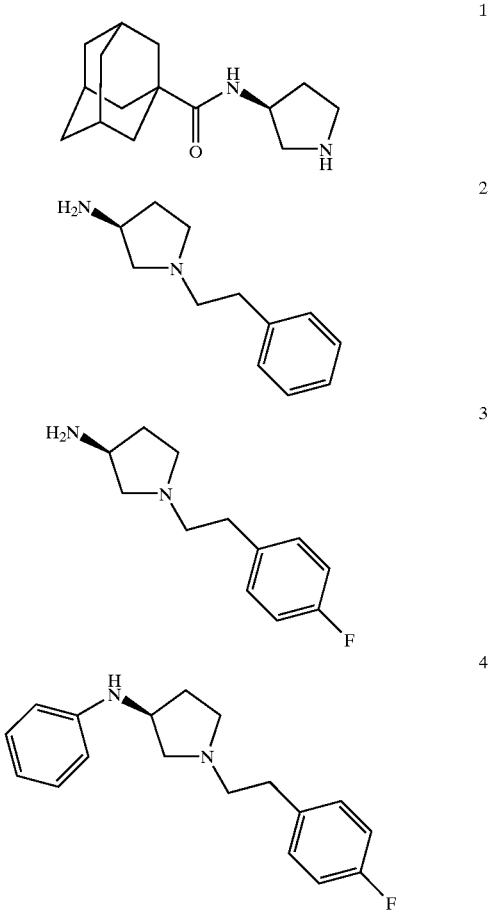

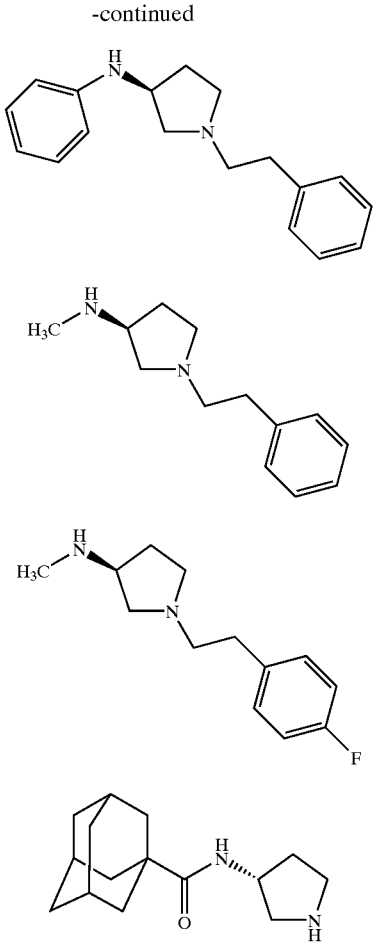

Example 1

(S)-N-(Pyrrolidin-3-yl)-1-adamantanecarboxamide (3.9 g) and 2-bromoethylbenzene (2.9 g) were dissolved in DMF, and potassium carbonate was added. The mixture was stirred under heating at 70° C. for 5 hours, and after the completion of the reaction, the solvent was evaporated under reduced pressure. Ethyl acetate was added to the obtained residue and the mixture was washed with saturated brine. The solvent was evaporated under reduced pressure, and the obtained residue was subjected to silica gel column chromatography (chloroform:methanol=30:1). The obtained eluate was concentrated and IPE was added. The precipitated crystals were collected by filtration to give (S)-N-(1-(2-phenylethyl)pyrrolidin-3-yl)-1-adamantanecarboxamide (4.3 g), melting point 119–121° C.

Example 2

(S)-N-(Pyrrolidin-3-yl)-1-adamantanecarboxamide (48 g) and 2-(4-fluorophenyl)ethyl p-toluenesulfonate (38 g) were reacted under the same conditions as in Example 1 to give (S)-N-(1-(2-(4-fluorophenyl)ethyl)pyrrolidin-3-yl)-1-adamantanecarboxamide (65 g), melting point 114–116° C. The obtained free basic compound (65 g) was dissolved in ethyl acetate, and 20% hydrochloric acid-isopropanol solution (35 g) was added thereto. After cooling, the precipitated crystals were collected by filtration to yield 57.4 g of crystals. The filtrate was concentrated under reduced pressure, ethyl acetate was added to the obtained residue. After cooling, the precipitated crystals were collected by filtration to yield 10.9 g of crystals. The obtained crystals were combined and recrystallized from a mixed solvent of ethanol (400 mL) and water (1500 mL) using activated carbon to give (S)-N-(1-(2-(4-fluorophenyl)ethyl)pyrrolidin-3-yl)-1-adamantanecarboxamide hydrochloride monohydrate (54 g), melting point 201–204° C.

$^1$H-NMR(DMSO-$d_6$) δ:1.58–2.05(16H,m), 2.05–2.45 (1H,m), 2.90–3.82(8H,m), 4.27–4.60(1H,m), 7.10–7.23(2H, m), 7.28–7.40(2H,m), 7.71–7.91(1H,m), 10.99–11.18(0.4H, m), 11.18–11.41(0.6H,m). Anal. Calcd. for $C_{23}H_{31}FN_2O \cdot HCl \cdot H_2O$:C,65.00; H,8.06; N,6.59. Found:C, 64.95; H,7.87; N,6.81.

Example 3

(S)-N-(Pyrrolidin-3-yl)-1-adamantanecarboxamide (0.38 g) and 2-(4-chlorophenyl)ethyl p-toluenesulfonate (0.57 g) were reacted under the same conditions as in Example 1 to give (S)-N-(1-(2-(4-chlorophenyl)ethyl)pyrrolidin-3-yl)-1-adamantanecarboxamide (0.13 g), melting point 94–95° C.

Example 4

(S)-N-(Pyrrolidin-3-yl)-1-adamantanecarboxamide (0.38 g) and 2-(4-methoxyphenyl)ethyl p-toluenesulfonate (0.56 g) were reacted under the same conditions as in Example 1 to give (S)-N-(1-(2-(4-methoxyphenyl)ethyl)pyrrolidin-3-yl)-1-adamantanecarboxamide (0.11 g), melting point 81–83° C.

Example 5

(S)-N-(Pyrrolidin-3-yl)-1-adamantanecarboxamide (0.5 g) and 2-(4-trifluoromethylphenyl)ethyl p-toluenesulfonate (0.69 g) were reacted under the same conditions as in Example 1. After the same post-treatment as in Example 1, the obtained compound was converted to hydrochloride with 30% hydrochloric acid-isopropanol to give (S)-N-(1-(2-(4-trifluoromethylphenyl)ethyl)pyrrolidin-3-yl)-1-adamantanecarboxamide hydrochloride 1/2 hydrate (0.51 g), melting point 214–215° C.

Example 6

(S)-N-(Pyrrolidin-3-yl)-1-adamantanecarboxamide (1.0 g) and 2-(4-cyanophenyl)ethyl p-toluenesulfonate (1.2 g) were dissolved in acetonitrile, and potassium carbonate was added thereto. The mixture was stirred under heating at 70° C. for 5 hours. After the completion of the reaction, the solvent was evaporated under reduced pressure. Ethyl acetate was added to the obtained residue and the mixture was washed with saturated brine. The solvent was evaporated under reduced pressure, and the obtained residue was subjected to silica gel column chromatography (chloroform:methanol=30:1). The obtained eluate was concentrated and IPE was added to the obtained residue. The precipitated crystals were collected by filtration to give (S)-N-(1-(2-(4-cyanophenyl)ethyl)pyrrolidin-3-yl)-1-adamantanecarboxamide (1.1 g), melting point 104–105° C.

Example 7

(S)-N-(1-(2-(4-Cyanophenyl)ethyl)pyrrolidin-3-yl)-1-adamantanecarboxamide was dissolved in 30% hydrochloric acid-ethanol and allowed to stand at 5° C. for 24 hours. The precipitated crystals were collected by filtration, dissolved in ammonia-ethanol, and refluxed under heating. After the completion of the reaction, the solvent was evaporated under reduced pressure, and the precipitated crystals were collected by filtration to give (S)-N-(1-(2-(4-amidinophenyl)ethyl)pyrrolidin-3-yl)-1-adamantanecarboxamide hydrochloride.

Example 8

(S)-N-(Pyrrolidin-3-yl)-1-adamantanecarboxamide and 2-(4-bromophenyl)ethyl p-toluenesulfonate were reacted under the same conditions as in Example 6 to give (S)-N-(1-(2-(4-bromophenyl)ethyl)pyrrolidin-3-yl)-1-adamantanecarboxamide.

Example 9

(S)-N-(Pyrrolidin-3-yl)-1-adamantanecarboxamide (0.5 g) and 2-(3-fluorophenyl)ethyl p-toluenesulfonate (0.59 g) were reacted under the same conditions as in Example 6 to give (S)-N-(1-(2-(3-fluorophenyl)ethyl)pyrrolidin-3-yl)-1-adamantanecarboxamide (0.22 g), melting point 87–89° C.

Example 10

(S)-N-(Pyrrolidin-3-yl)-1-adamantanecarboxamide (0.5 g) and 2-(2-fluorophenyl)ethyl p-toluenesulfonate (0.59 g) were reacted under the same conditions as in Example 6 to give (S)-N-(1-(2-(2-fluorophenyl)ethyl)pyrrolidin-3-yl)-1-adamantanecarboxamide (0.22 g), melting point 106–108° C.

Example 11

(S)-N-(Pyrrolidin-3-yl)-1-adamantanecarboxamide (0.5 g) and 2-(3-trifluoromethylphenyl)ethyl p-toluenesulfonate (0.69 g) were reacted under the same conditions as in Example 1. After the same post-treatment as in Example 1, the obtained compound was converted to hydrochloride with 30% hydrochloric acid-isopropanol to give (S)-N-(1-(2-(3-trifluoromethylphenyl)ethyl)pyrrolidin-3-yl)-1-adamantanecarboxamide hydrochloride monohydrate (0.44 g), melting point 160–163° C.

Example 12

(S)-N-(Pyrrolidin-3-yl)-1-adamantanecarboxamide (0.5 g) and 2-(2-trifluoromethylphenyl)ethyl p-toluenesulfonate (0.69 g) were reacted under the same conditions as in Example 1. After the same post-treatment as in Example 1, the obtained compound was converted to hydrochloride with 30% hydrochloric acid-isopropanol to give (S)-N-(1-(2-(2-trifluoromethylphenyl)ethyl)pyrrolidin-3-yl)-1-adamantanecarboxamide hydrochloride 1 hydrate (0.44 g), melting point 127–128° C.

Example 13

(S)-3-Amino-1-benzylpyrrolidine (10 g) and triethylamine (24 ml) were dissolved in DMF (100 ml). Under ice-cooling, 1-adamantanecarbonyl chloride (12.4 g) was added thereto, and the mixture was stirred overnight at room temperature. The solvent was evaporated under reduced pressure. To the obtained residue was added ethyl acetate and the mixture was washed with saturated brine. The solvent was evaporated under reduced pressure, and the obtained residue was subjected to silica gel column chromatography (chloroform:methanol=30:1). The obtained eluate was concentrated and IPE was added to the obtained residue. The precipitated crystals were collected by filtration to give (S)-N-(1-benzylpyrrolidin-3-yl)-1-adamantanecarboxamide (14.8 g), melting point 130–132° C.

Example 14

(S)-N-(Pyrrolidin-3-yl)-1-adamantanecarboxamide (0.38 g) and 3-bromopropylbenzene (0.37 g) were reacted under the same conditions as in Example 1 to give (S)-N-(1-(3-phenylpropyl)pyrrolidin-3-yl)-1-adamantanecarboxamide (0.12 g), melting point 118–120° C.

Example 15

(S)-N-(Pyrrolidin-3-yl)-1-adamantanecarboxamide (0.5 g) and 3-(4-fluorophenyl)propyl p-toluenesulfonate (0.92 g) were reacted under the same conditions as in Example 6 to give (S)-N-(1-(3-(4-fluorophenyl)propyl)pyrrolidin-3-yl)-1-adamantanecarboxamide (0.15 g), melting point 114–115° C.

Example 16

(S)-N-(Pyrrolidin-3-yl)-1-adamantanecarboxamide (0.5 g) and 3-(4-chlorophenyl)propyl p-toluenesulfonate (0.97 g) were reacted under the same conditions as in Example 6 to give (S)-N-(1-(3-(4-chlorophenyl)propyl)pyrrolidin-3-yl)-1-adamantanecarboxamide (0.26 g), melting point 117–119° C.

Example 17

(S)-N-(Pyrrolidin-3-yl)-1-adamantanecarboxamide (0.38 g) and 4-bromobutylbenzene (0.39 g) were reacted under the same conditions as in Example 1 to give (S)-N-(1-(4-phenylbutyl)pyrrolidin-3-yl)-1-adamantanecarboxamide (0.073 g), melting point 82–84° C.

Example 18

(S)-N-(Pyrrolidin-3-yl)-1-adamantanecarboxamide (0.5 g) and (2,3-dihydroinden-2-yl)methyl p-toluenesulfonate (0.91 g) were reacted under the same conditions as in Example 6. After the same post-treatment as in Example 6, the obtained compound was converted to hydrochloride with 30% hydrochloric acid-isopropanol to give (S)-N-(1-((2,3-dihydroinden-2-yl)methyl)pyrrolidin-3-yl)-1-adamantanecarboxamide hydrochloride 1 hydrate (0.45 g), melting point 241–243° C.

Example 19

(S)-N-(Pyrrolidin-3-yl)-1-adamantanecarboxamide and (2,3-dihydroinden-1-yl)methyl p-toluenesulfonate were reacted under the same conditions as in Example 6 to give (S)-N-(1-((2,3-dihydroinden-1-yl)methyl)pyrrolidin-3-yl)-1-adamantanecarboxamide.

Example 20

(S)-N-(Pyrrolidin-3-yl)-1-adamantanecarboxamide and (1,2,3,4-tetrahydronaphthalen-1-yl)methyl p-toluenesulfonate were reacted under the same conditions as in Example 6 to give (S)-N-(1-((1,2,3,4-tetrahydronaphthalen-1-yl)methyl)pyrrolidin-3-yl)-1-adamantanecarboxamide hydrochloride 5/4 hydrate, melting point 140–142° C.

Example 21

(S)-N-(Pyrrolidin-3-yl)-1-adamantanecarboxamide and (1,2,3,4-tetrahydronaphthalen-2-yl)methyl p-toluenesulfonate were reacted under the same conditions as in Example 6 to give (S)-N-(1-((1,2,3,4-tetrahydronaphthalen-2-yl)methyl)pyrrolidin-3-yl)-1-adamantanecarboxamide.

Example 22

(S)-N-(Pyrrolidin-3-yl)-1-adamantanecarboxamide (1.0 g), 2-indanone (0.7 g), and a catalytic amount of p-toluenesulfonamide were dissolved in toluene (20 ml), and the mixture was refluxed overnight under heating with Dean-Stark trap. The solvent was evaporated under reduced pressure, and the obtained residue was dissolved in methanol (20 ml). Sodium borohydride (0.6 g) was added under ice-cooling. After the completion of the reaction, the solvent was evaporated under reduced pressure. Water was added to the obtained residue, and the mixture was extracted with chloroform and dried over magnesium sulfate. The solvent was evaporated under reduced pressure, and the obtained residue was subjected to silica gel column chromatography (chloroform:methanol=20:1). The obtained eluate was concentrated and dissolved in ethyl acetate, and 30% isopropanol-hydrochloric acid was added thereto. The precipitated crystals were collected by filtration to give (S)-N-(1-(2,3-dihydroinden-2-yl)pyrrolidin-3-yl)-1-adamantanecarboxamide hydrochloride 1/10 hydrate (0.53 g), melting point 278–279° C.

Example 23

Diphenylacetic acid (0.75 g) and (S)-3-amino-1-(2-phenylethyl)pyrrolidine (0.67 g) were dissolved in DMF (10 ml), and triethylamine (1.4 ml) was added thereto, which was followed by addition of diethyl cyanophosphate (0.67 ml) under ice-cooling. After completion of the reaction, the solvent was evaporated under reduced pressure. The obtained residue was dissolved in ethyl acetate, washed successively with an aqueous potassium carbonate solution and saturated brine, and dried over magnesium sulfate. The solvent was evaporated under reduced pressure, and the obtained residue was subjected to silica gel column chromatography (chloroform:methanol=30:1). The obtained eluate was concentrated to give (S)-N-(1-(2-phenylethyl)pyrrolidin-3-yl)diphenylacetamide (0.77 g). The obtained compound was dissolved in acetone (3 ml), and a solution of oxalic acid (0.18 g) in acetone (3 ml) was added thereto. The precipitated crystals were collected by filtration and washed with acetone to give (S)-N-(1-(2-phenylethyl)pyrrolidin-3-yl)diphenylacetamide oxalate, melting point 191–192° C.

Example 24

Diphenylacetic acid and (S)-3-amino-1-(2-(4-fluorophenyl)ethyl)pyrrolidine were reacted under the same conditions as in Example 23 to give (S)-N-(1-(2-(4-fluorophenyl)ethyl)pyrrolidin-3-yl)diphenylacetamide oxalate 1/4 hydrate, melting point 156–158° C.

Example 25

Dicyclohexylacetic acid and (S)-3-amino-1-(2-phenylethyl)pyrrolidine were reacted under the same conditions as in Example 23 to give (S)-N-(1-(2-phenylethyl)pyrrolidin-3-yl)dicyclohexylacetamide.

Example 26

Dicyclohexylacetic acid (0.45 g) and (S)-3-amino-1-(2-(4-fluorophenyl)ethyl)pyrrolidine (0.42 g) were reacted under the same conditions as in Example 23 to give (S)-N-(1-(2-(4-fluorophenyl)ethyl)pyrrolidin-3-yl)dicyclohexylacetamide (0.22 g), melting point 122–124° C.

Example 27

2-Cyclopentylphenylacetic acid (0.39 g) and (S)-3-amino-1-(2-phenylethyl)pyrrolidine (0.3 g) were reacted under the same conditions as in Example 23 to give N-((S)-1-(2-phenylethyl)pyrrolidin-3-yl)-2-cyclopentylphenylacetamide (0.13 g), melting point 117–119° C.

Example 28

2-Cyclopentylphenylacetic acid and (S)-3-amino-1-(2-(4-fluorophenyl)ethyl)pyrrolidine were reacted under the same conditions as in Example 23 to give N-((S)-1-(2-(4-fluorophenyl)ethyl)pyrrolidin-3-yl)-2-cyclopentylphenylacetamide.

Example 29

Fluorene-9-carboxylic acid and (S)-3-amino-1-(2-phenylethyl)pyrrolidine were reacted under the same conditions as in Example 23 to give (S)-N-(1-(2-phenylethyl)pyrrolidin-3-yl)-1-fluorene-9-carboxamide.

Example 30

Fluorene-9-carboxylic acid and (S)-3-amino-1-(2-(4-fluorophenyl)ethyl)pyrrolidine were reacted under the same conditions as in Example 23 to give (S)-N-(1-(2-(4-fluorophenyl)ethyl)pyrrolidin-3-yl)-1-fluorene-9-carboxamide oxalate, melting point 152–154° C.

Example 31

9,10-Dihydroanthracene-9-carboxylic acid and (S)-3-amino-1-(2-phenylethyl)pyrrolidine were reacted under the same conditions as in Example 23 to give (S)-N-(1-(2-phenylethyl)pyrrolidin-3-yl)-9,10-dihydroanthracene-9-carboxamide.

Example 32

9,10-Dihydroanthracene-9-carboxylic acid and (S)-3-amino-1-(2-(4-fluorophenyl)ethyl)pyrrolidine were reacted under the same conditions as in Example 23 to give (S)-N-(1-(2-(4-fluorophenyl)ethyl)pyrrolidin-3-yl)-9,10-dihydroanthracene-9-carboxamide.

Example 33

10,11-Dihydro-dibenzo[a,d]cycloheptene-5-carboxylic acid and (S)-3-amino-1-(2-phenylethyl)pyrrolidine were reacted under the same conditions as in Example 23 to give (S)-N-(1-(2-phenylethyl)pyrrolidin-3-yl)-10,11-dihydro-dibenzo[a,d]cycloheptene-5-carboxamide.

Example 34

10,11-Dihydro-dibenzo[a,d]cycloheptene-5-carboxylic acid (0.57 g) and (S)-3-amino-1-(2-(4-fluorophenyl)ethyl)pyrrolidine (0.42 g) were reacted under the same conditions as in Example 23 to give (S)-N-(1-(2-(4-fluorophenyl)ethyl)pyrrolidin-3-yl)-10,11-dihydro-dibenzo[a,d]cycloheptene-5-carboxamide. The obtained compound was dissolved in acetone (3 ml), and a solution of oxalic acid in acetone was added thereto. The precipitated crystals were collected by filtration and washed with acetone to give (S)-N-(1-(2-(4-fluorophenyl)ethyl)pyrrolidin-3-yl)-10,11-dihydrodibenzo[a,d]cycloheptene-5-carboxamide oxalate (0.24 g), melting point 178–179° C.

Example 35

Dibenzo[a,d]cycloheptene-5-carboxylic acid and (S)-3-amino-1-(2-phenylethyl)pyrrolidine were reacted under the same conditions as in Example 23 to give (S)-N-(1-(2-phenylethyl)pyrrolidin-3-yl)dibenzo[a,d]cycloheptene-5-carboxamide.

Example 36

Dibenzo[a,d]cycloheptene-5-carboxylic acid and (S)-3-amino-1-(2-(4-fluorophenyl)ethyl)pyrrolidine were reacted under the same conditions as in Example 23 to give (S)-N-(1-(2-(4-fluorophenyl)ethyl)pyrrolidin-3-yl)dibenzo[a,d]cycloheptene-5-carboxamide, melting point 127–128° C.

Example 37

9-Xanthenylcarboxylic acid and (S)-3-amino-1-(2-phenylethyl)pyrrolidine were reacted under the same conditions as in Example 23 to give (S)-N-(1-(2-phenylethyl)pyrrolidin-3-yl)-9-xanthenylcarboxamide.

Example 38

9-Xanthenylcarboxylic acid and (S)-3-amino-1-(2-(4-fluorophenyl)ethyl)pyrrolidine were reacted under the same conditions as in Example 23 to give (S)-N-(1-(2-(4-fluorophenyl)ethyl)pyrrolidin-3-yl)-9-xanthenylcarboxamide.

Example 39

9-Thioxanthenylcarboxylic acid and (S)-3-amino-1-(2-phenylethyl)pyrrolidine were reacted under the same conditions as in Example 23 to give (S)-N-(1-(2-phenylethyl)pyrrolidin-3-yl)-9-thioxanthenylcarboxamide.

Example 40

9-Thioxanthenylcarboxylic acid and (S)-3-amino-1-(2-(4-fluorophenyl)ethyl)pyrrolidine were reacted under the same conditions as in Example 23 to give (S)-N-(1-(2-(4-fluorophenyl)ethyl)pyrrolidin-3-yl)-9-thioxanthenylcarboxamide.

Example 41

Bis(2-pyridyl)acetic acid and (S)-3-amino-1-(2-phenylethyl)pyrrolidine were reacted under the same conditions as in Example 23 to give (S)-N-(1-(2-phenylethyl)pyrrolidin-3-yl)bis(2-pyridyl)acetamide.

Example 42

Bis(2-pyridyl)acetic acid and (S)-3-amino-1-(2-(4-fluorophenyl)ethyl)pyrrolidine were reacted under the same conditions as in Example 23 to give (S)-N-(1-(2-(4-fluorophenyl)ethyl)pyrrolidin-3-yl)bis(2-pyridyl)acetamide.

Example 43

2-(2-pyridyl)phenylacetic acid and (S)-3-amino-1-(2-phenylethyl)pyrrolidine were reacted under the same conditions as in Example 23 to give (S)-N-(1-(2-phenylethyl)pyrrolidin-3-yl)-2-(2-pyridyl)phenylacetamide.

Example 44

2-(2-Pyridyl)phenylacetic acid and (S)-3-amino-1-(2-(4-fluorophenyl)ethyl)pyrrolidine were reacted under the same conditions as in Example 23 to give (S)-N-(1-(2-(4-fluorophenyl)ethyl)pyrrolidin-3-yl)-2-(2-pyridyl)phenylacetamide.

Example 45

Diphenylamine was dissolved in THF, and 1,1'-carbonylbis-1H-imidazole was added thereto. The mixture was stirred overnight at room temperature. The solvent was evaporated under reduced pressure. To the obtained residue was added (S)-3-amino-1-(2-phenylethyl)pyrrolidine and toluene, and the mixture was refluxed under heating. After the completion of the reaction, the reaction mixture was washed successively with an aqueous potassium carbonate solution and saturated brine, and dried over magnesium sulfate. The solvent was evaporated under reduced pressure, and the obtained residue was purified by silica gel chromatography to give (S)-1,1-diphenyl-3-(1-(2-phenylethyl)pyrrolidin-3-yl)urea.

Example 46

Diphenylamine and (S)-3-amino-1-(2-(4-fluorophenyl)ethyl)pyrrolidine were reacted under the same conditions as in Example 45 to give (s)-1,1-diphenyl-3-(1-(2-(4-fluorophenyl)ethyl)pyrrolidin-1-yl)urea.

Example 47

Dicyclohexylamine and (S)-3-amino-1-(2-phenylethyl)pyrrolidine were reacted under the same conditions as in Example 45 to give (S)-1,1-dicyclohexyl-3-(1-(2-phenylethyl)pyrrolidin-3-yl)urea.

Example 48

Dicyclohexylamine (0.48 g) and (S)-3-amino-1-(2-(4-fluorophenyl)ethyl)pyrrolidine (0.5 g) were reacted under the same conditions as in Example 45 to give (S)-1,1-dicyclohexyl-3-(1-(2-(4-fluorophenyl)ethyl)pyrrolidin-3-yl)urea (0.064 g), melting point 97–98° C.

Example 49

5,6-Dihydro-11H-dibenz[b,f]azepine and (S)-3-amino-1-(2-phenylethyl)pyrrolidine were reacted under the same conditions as in Example 45 to give 11-(1-(2-phenylethyl)pyrrolidin-3-yl)carbamoyl-5,6-dihydro-11H-dibenz[b,f]azepine.

Example 50

5,6-Dihydro-11H-dibenz[b,f]azepine and (S)-3-amino-1-(2-(4-fluorophenyl)ethyl)pyrrolidine were reacted under the same conditions as in Example 45 to give 11-(1-(2-(4-fluorophenyl)ethyl)pyrrolidin-3-yl)carbamoyl-5,6-dihydro-11H-dibenz[b,f]azepine.

Example 51

1-Aminoadamantane (0.4 g) was dissolved in THF (10 ml), 1,1'-carbonylbis-1H-imidazole (0.6 g) was added thereto, and the mixture was stirred overnight at room temperature. The solvent was evaporated under reduced pressure. To the obtained residue was added (S)-3-amino-1-(2-phenylethyl)pyrrolidine (0.5 g) and toluene (10 ml), and the mixture was refluxed under heating for 6 hours. After the completion of the reaction, to the reaction mixture was added ethyl acetate, washed successively with an aqueous potassium carbonate solution and saturated brine, and dried over magnesium sulfate. The solvent was evaporated under reduced pressure, and the obtained residue was subjected to silica gel chromatography (chloroform:methanol= 20:1). The obtained eluate was concentrated. Acetone (3 ml) was added to the obtained residue, and further, 30% isopropanol-hydrochloric acid. The precipitated crystals were collected by filtration to give (S)-1-(1-adamantyl)-3-(1-(2-phenylethyl)pyrrolidin-3-yl)urea hydrochloride 1/5 hydrate, melting point 201–202° C.

Example 52

1-Aminoadamantane and (S)-3-amino-1-(2-(4-fluorophenyl)ethyl)pyrrolidine were reacted under the same conditions as in Example 51 to give (S)-1-(1-adamantyl)-3-(1-(2-(4-fluorophenyl)ethyl)pyrrolidin-3-yl)urea.

Example 53

3-Anilino-1-(2-phenylethyl)pyrrolidine was dissolved in DMF, and triethylamine was added thereto. 1-Adamantanecarbonyl chloride was further added under ice-cooling. After the completion of the reaction, ethyl acetate was added to the reaction mixture, and the mixture was washed successively with an aqueous potassium carbonate solution and saturated brine, and dried over magnesium sulfate. The solvent was evaporated under reduced pressure, and the obtained residue was subjected to silica gel chromatography to N-phenyl-N-(1-(2-phenylethyl)pyrrolidin-3-yl)-1-adamantanecarboxamide.

Example 54

3-Anilino-1-(2-(4-fluorophenyl)ethyl)pyrrolidine and 1-adamantanecarbonyl chloride were reacted under the same conditions as in Example 53 to give N-phenyl-N-(1-(2-(4-fluorophenyl)ethyl)pyrrolidin-3-yl)-1-adamantanecarboxamide.

Example 55

(S)-N-Methyl-N-(pyrrolidin-3-yl)-1-adamantanecarboxamide and (2-bromoethyl)benzene were reacted under the same conditions as in Example 1 to give (S)-N-methyl-N-(1-(2-phenylethyl)pyrrolidin-3-yl)-1-adamantanecarboxamide.

Example 56

(S)-N-Methyl-N-(pyrrolidin-3-yl)-1-adamantanecarboxamide (0.5 g) and 2-(4-fluorophenyl)ethyl p-toluenesulfonate (0.6 g) were reacted under the same conditions as in Example 1 to give (S)-N-methyl-N-(1-(2-(4-fluorophenyl)ethyl)pyrrolidin-3-yl)-1-adamantanecarboxamide hydrochloride 1/2 hydrate (0.3 g), melting point 253–254° C.

Example 57

7-Norbornadienecarboxylic acid and (S)-3-amino-1-(2-phenylethyl)pyrrolidine were reacted under the same conditions as in Example 23 to give (S)-N-(1-(2-phenylethyl)pyrrolidin-3-yl)-7-norbornadienecarboxamide.

Example 58

7-Norbornadienecarboxylic acid and (S)-3-amino-1-(2-(4-fluorophenyl)ethyl)pyrrolidine were reacted under the same conditions as in Example 23 to give (S)-N-(1-(2-(4-fluorophenyl)ethyl)pyrrolidin-3-yl)-7-norbornadienecarboxamide.

Example 59

7-Norbornanecarboxylic acid and (S)-3-amino-1-(2-phenylethyl)pyrrolidine were reacted under the same conditions as in Example 23 to give (S)-N-(1-(2-phenylethyl)pyrrolidin-3-yl)-7-norbornanecarboxamide.

Example 60

7-Norbornanecarboxylic acid and (S)-3-amino-1-(2-(4-fluorophenyl)ethyl)pyrrolidine were reacted under the same conditions as in Example 23 to give (S)-N-(1-(2-(4-fluorophenyl)ethyl)pyrrolidin-3-yl)-7-norbornanecarboxamide.

Example 61

1-Cyclohexyl-1-cyclopentanecarboxylic acid and (S)-3-amino-1-(2-phenylethyl)pyrrolidine were reacted under the same conditions as in Example 23 to give (S)-N-(1-(2-phenylethyl)pyrrolidin-3-yl)-1-cyclohexyl-1-cyclopentanecarboxamide.

Example 62

1-Cyclohexyl-1-cyclopentanecarboxylic acid and (S)-3-amino-1-(2-(4-fluorophenyl)ethyl)pyrrolidine were reacted under the same conditions as in Example 23 to give (S)-N-(1-(2-(4-fluorophenyl)ethyl)pyrrolidin-3-yl)-1-cyclohexyl-1-cyclopentanecarboxamide.

Example 63

(R)-N-(Pyrrolidin-3-yl)-1-adamantanecarboxamide (0.38 g) and 2-bromobenzene (0.3 g) were reacted under the same conditions as in Example 1 to give (R)-N-(1-(2-phenylethyl)pyrrolidin-3-yl)-1-adamantanecarboxamide (0.22 g), melting point 118–120° C.

Example 64

(R)-N-(Pyrrolidin-3-yl)-1-adamantanecarboxamide and 2-(4-fluorophenyl)ethyl p-toluenesulfonate were reacted under the same conditions as in Example 1 to give (R)-N-(1-(2-(4-fluorophenyl)ethyl)pyrrolidin-3-yl)-1-adamantanecarboxamide.

Example 65

(S)-N-Methyl-N-(pyrrolidin-3-yl)-1-adamantanecarboxamide (0.5 g) and 2-(3-fluorophenyl)ethyl p-toluenesulfonate (0.6 g) ere reacted under the same conditions as in Example 1 to give (S)-N-methyl-N-(1-(2-(3-fluorophenyl)ethyl)pyrrolidin-3-yl)-1-adamantanecarboxamide hydrochloride 1/2 hydrate (0.3 g), melting point 252–253° C.

Example 66

(S)-N-Methyl-N-(pyrrolidin-3-yl)-1-adamantanecarboxamide (0.5 g) and 2-(2-fluorophenyl)ethyl p-toluenesulfonate (0.6 g) were reacted under the same conditions as in Example 1 to give (S)-N-methyl-N-(1-(2-(2-fluorophenyl)ethyl)pyrrolidin-3-yl)-1-adamantanecarboxamide hydrochloride (0.3 g), melting point 241–242° C.

Example 67

2,2-Bis(4-fluorophenyl)acetyl chloride (0.74 g) and (S)-3-amino-1-(2-(4-fluorophenyl)ethyl)pyrrolidine (0.42 g) were reacted under the same conditions as in Example 53 to give (S)-2,2-bis(4-fluorophenyl)-N-(1-(2-(4-fluorophenyl)ethyl)pyrrolidin-3-yl)-1-acetamide (0.2 g), melting point 112–114° C.

Example 68

(R)-3-Methylamino-1-(2-(4-fluorophenyl)ethyl)pyrrolidine (0.66 g) and 1-adamantanecarbonyl chloride (0.6 g) were reacted under the same conditions as in Example 53 to give (R)-N-methyl-N-(1-(2-(4-fluorophenyl)ethyl)

Example 69

(S)-3-Amino-1-(2-(4-fluorophenyl)ethyl)pyrrolidine (0.62 g) was dissolved in THF (10 ml), and 1,1'-carbonylbis-1H-imidazole (0.49 g) was added thereto at room temperature. The mixture was stirred for 1 hour, and the solvent was evaporated under reduced pressure. 4-Azatricyclo[4.3.1.1(3,8)]undecane (0.45 g) and toluene (10 ml) were added to the obtained residue, and the mixture was refluxed under heating for 0.5 hour. The reaction mixture was cooled to room temperature. Water was added thereto, and the organic layer was separated and dried over magnesium sulfate. The solvent was evaporated under reduced pressure, the obtained residue was subjected to silica gel column chromatography (chloroform:methanol=20:1). The obtained eluate was concentrated and the obtained residue was dissolved in ethyl acetate. 30% Isopropanol-hydrochloric acid was added thereto. The precipitated crystals were collected by filtration to give (S)-N-(1-(2-(4-fluorophenyl)ethyl)pyrrolidin-3-yl)-(4-azatricyclo[4.3.1.1(3,8)]undecan-4-yl)carboxamide hydrochloride 1 hydrate (0.53 g), melting point 110–113° C./decomposition.

Example 70

(S)-N-(Pyrrolidin-3-yl)-1-adamantanecarboxamide (0.74 g) and (R)-styrene oxide (0.4 g) were dissolved in ethanol (10 ml), and the mixture was refluxed under heating for 4 hours. The solvent was evaporated under reduced pressure, and the obtained residue was subjected to silica gel column chromatography (NH silica gel: Fuji Silysia Chemical Ltd., hexane:ethyl acetate=1:1). The obtained eluate was concentrated and the residue was dissolved in ethyl acetate. 30% Isopropanol-hydrochloric acid was added thereto, and the precipitated crystals were collected by filtration to give (S)-N-(1-((R)-2-hydroxy-2-phenylethyl)pyrrolidin-3-yl)-1-adamantanecarboxamide hydrochloride monohydrate (0.43 g), melting point 139–141° C.

Example 71

(S)-N-(Pyrrolidin-3-yl)-1-adamantanecarboxamide (0.74 g) and (S)-styrene oxide (0.4 g) were reacted under the same conditions as in Example 71 to give (S)-N-(1-((S)-2-hydroxy-2-phenylethyl)pyrrolidin-3-yl)-1-adamantanecarboxamide hydrochloride 1/5 hydrate (0.40 g), melting point 149–151° C.

Example 72

(S)-3-Amino-1-(2-(4-fluorophenyl)ethyl)pyrrolidine (0.42 g) and triethylamine (0.28 ml) were dissolved in methylene chloride (10 ml), and carbazole-N-carbonyl chloride (0.46 g) was added under ice-cooling. After the completion of the reaction, water was added, and the mixture was extracted with chloroform and dried over magnesium sulfate. The solvent was evaporated under reduced pressure, and IPE was added to the obtained residue. The precipitated crystals were collected by filtration to give (S)-N-(1-(2-(4-fluorophenyl)ethyl)pyrrolidin-3-yl)carbazole-9-carboxamide (0.38 g), melting point 107–108° C.

Example 73

2,2-Di(2-thienyl)acetyl chloride (0.67 g) and (S)-3-amino-1-(2-(4-fluorophenyl)ethyl)pyrrolidine (0.42 g) were reacted under the same conditions as in Example 53 to give (S)-2,2-di(2-thienyl)-N-(1-(2-(4-fluorophenyl)ethyl)pyrrolidin-3-yl)acetamide (0.2 g), melting point 96–98° C.

Example 74

2,2-Bis(2-fluorophenyl)acetyl chloride (0.74 g) and (S)-3-amino-1-(2-(4-fluorophenyl)ethyl)pyrrolidine (0.42 g) were reacted under the same conditions as in Example 53 to give (S)-2,2-bis(2-fluorophenyl)-N-(1-(2-(4-fluorophenyl)ethyl)pyrrolidin-3-yl)acetamide (0.29 g), melting point 107–108° C.

Example 75

2,2-Bis(2-methylphenyl)acetyl chloride (0.74 g) and (S)-3-amino-1-(2-(4-fluorophenyl)ethyl)pyrrolidine (0.42 g) were reacted under the same conditions as in Example 53 to give (S)-2,2-bis(2-methylphenyl)-N-(1-(2-(4-fluorophenyl)ethyl)pyrrolidin-3-yl)acetamide (0.13 g), melting point 108–110° C.

The structural formulas of the compounds obtained in the above-mentioned Examples 1–75 are respectively as follows.

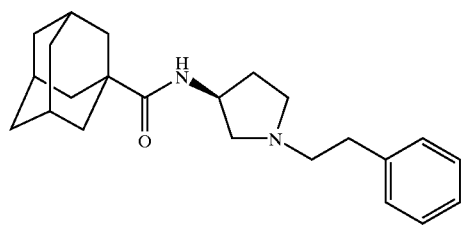

1

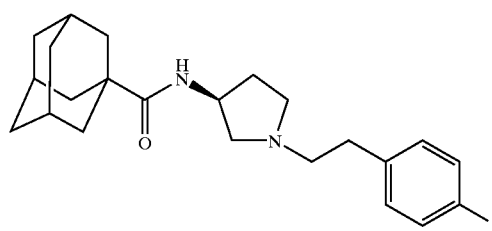

2

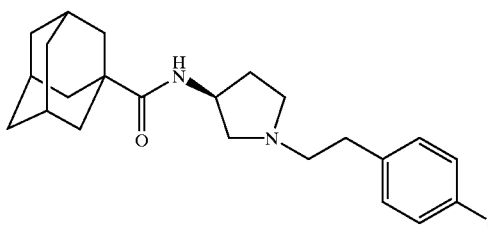

3

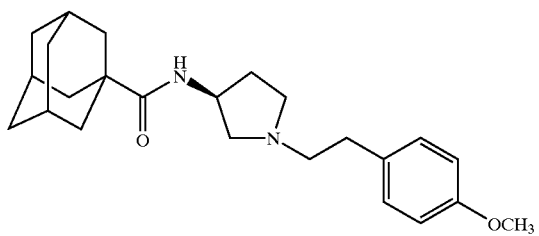

4

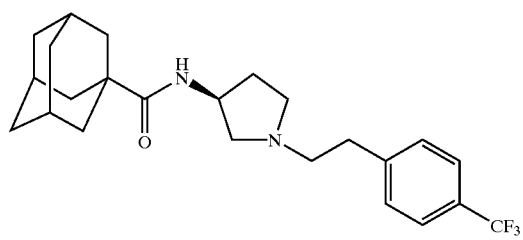
5
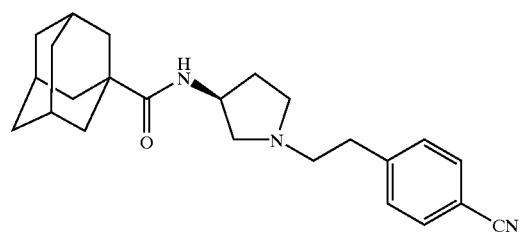
6
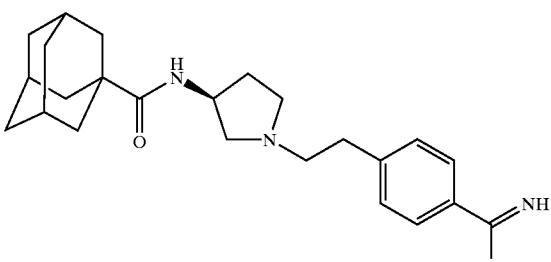
7
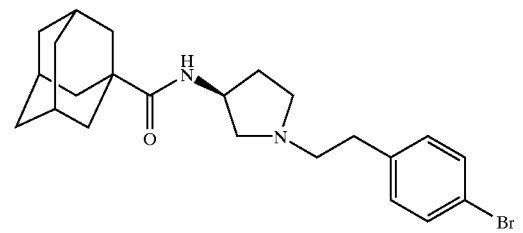
8
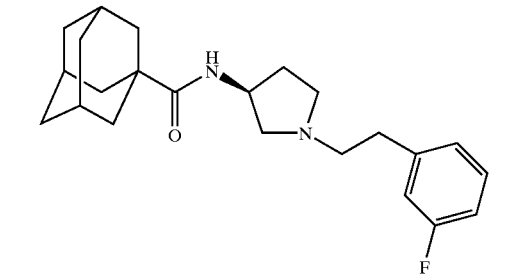
9
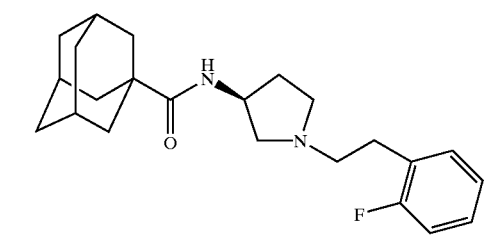
10
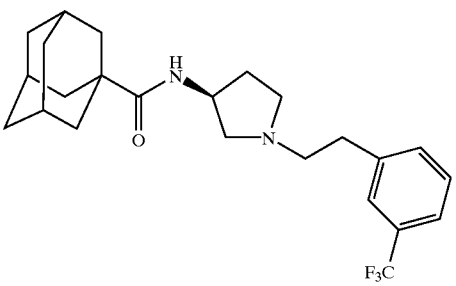
11
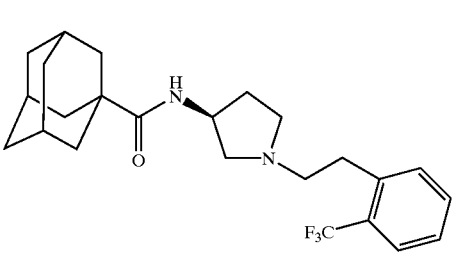
12
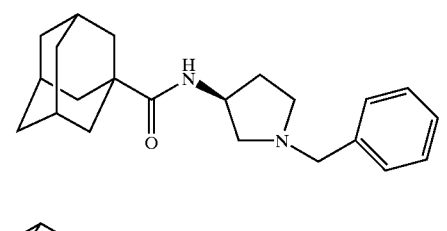
13
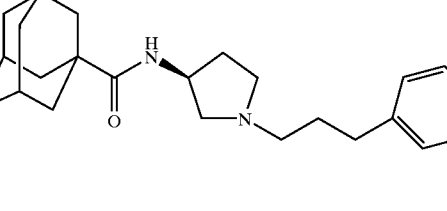
14
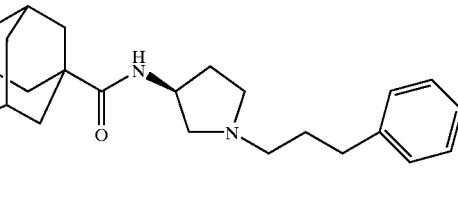
15
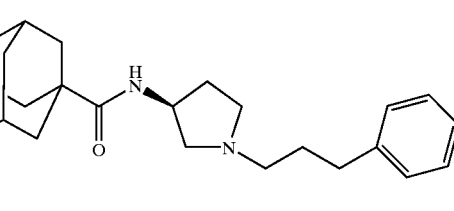
16
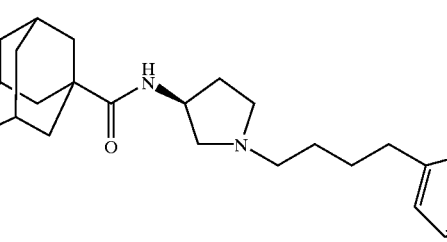
17

18
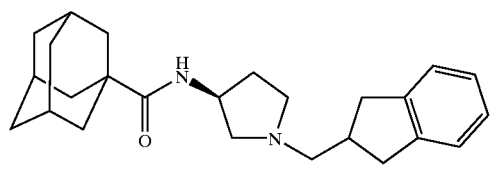
19
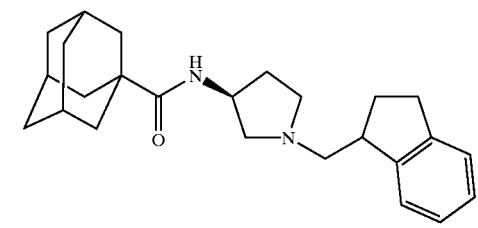
20
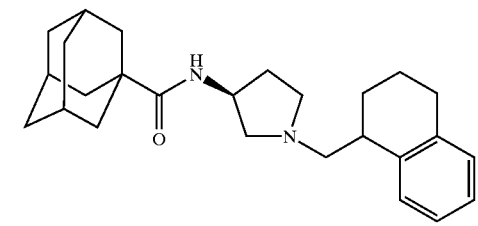
21
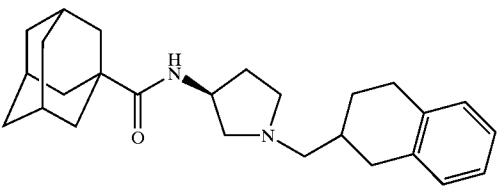
22
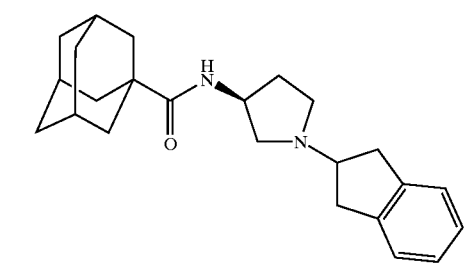
23
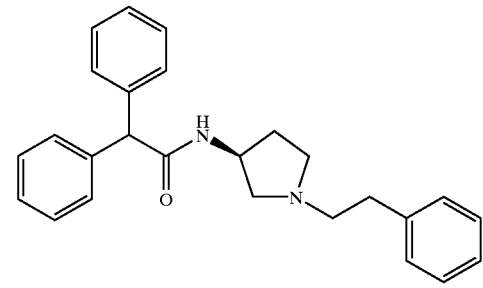
24
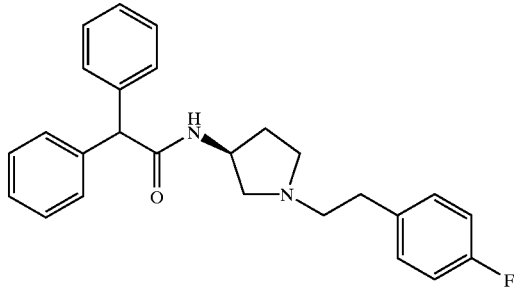
25
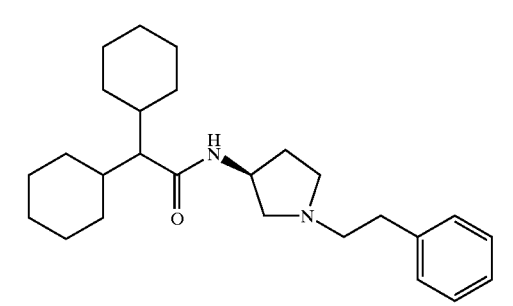
26
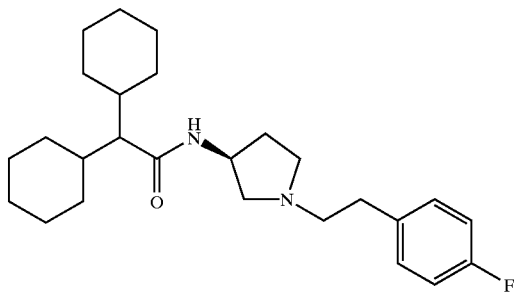
27
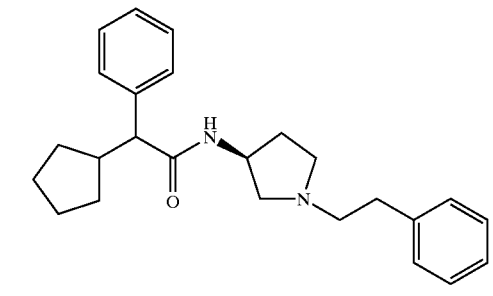
28
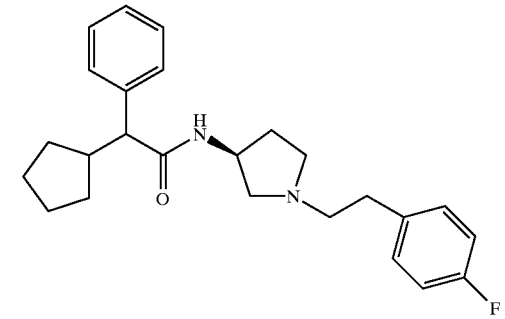

29
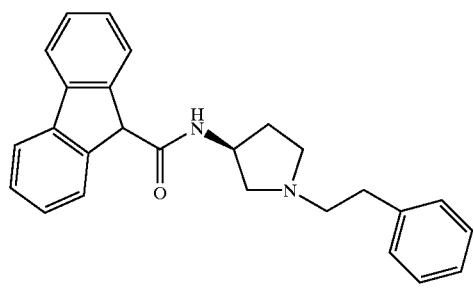
30
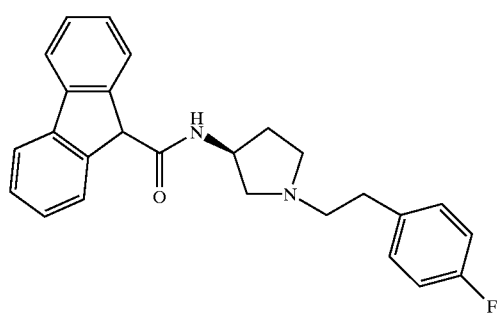
31
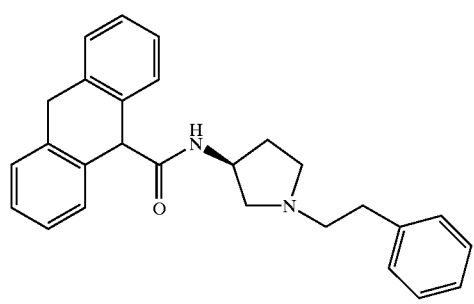
32
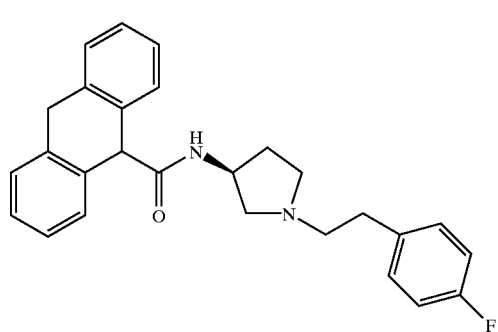
33
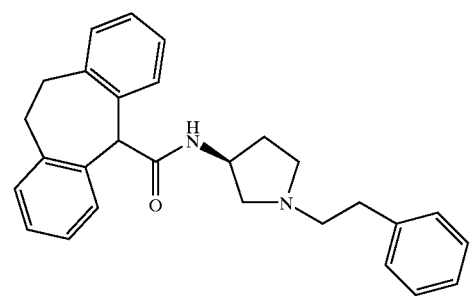
34
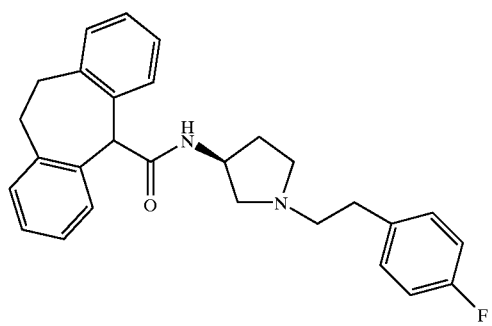
35
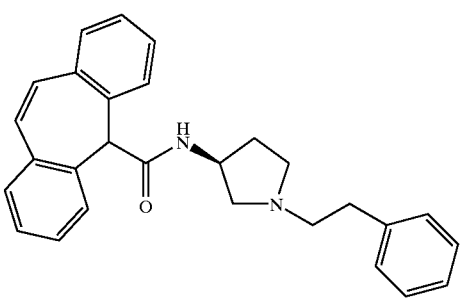
36
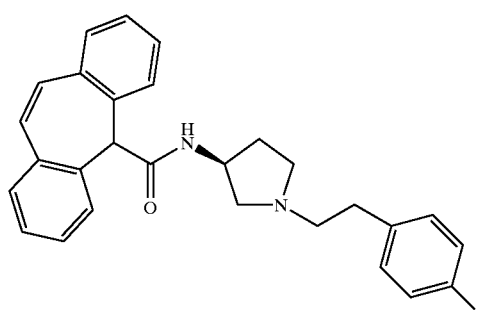
37
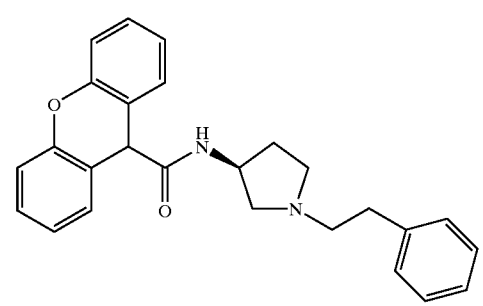
38
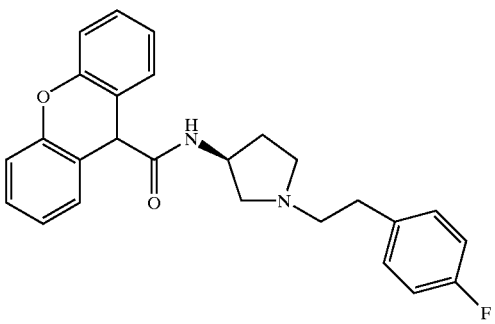

39
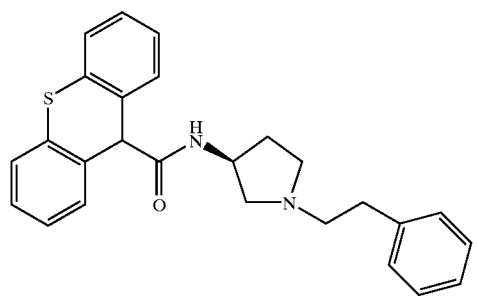
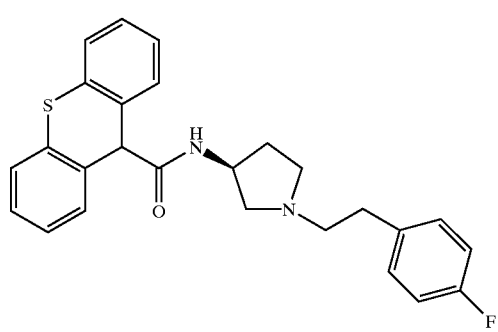
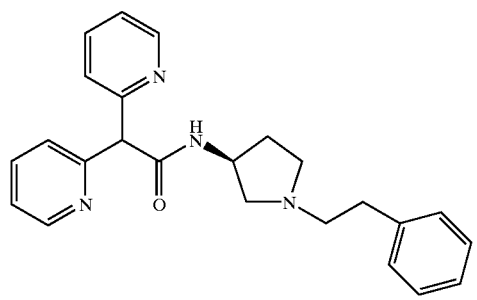
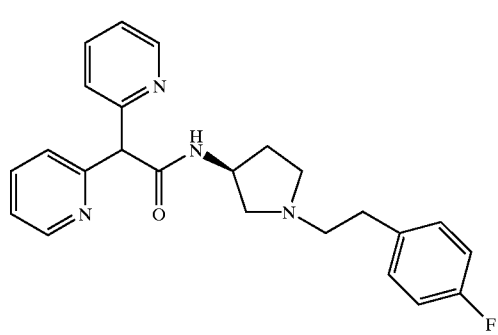
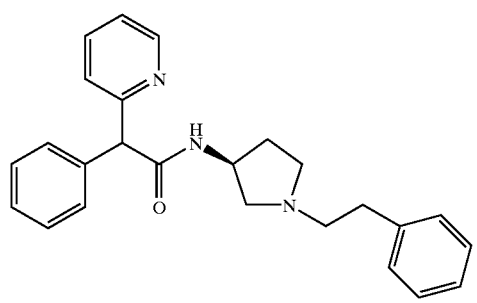
40
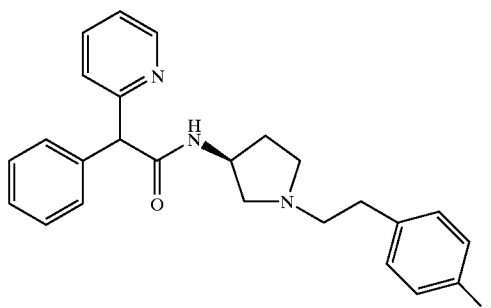
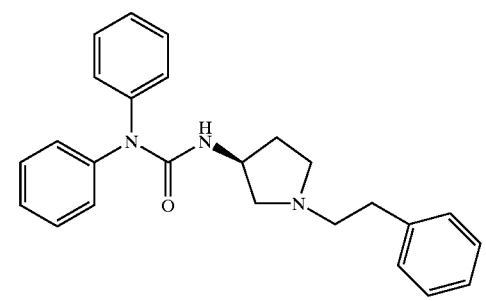
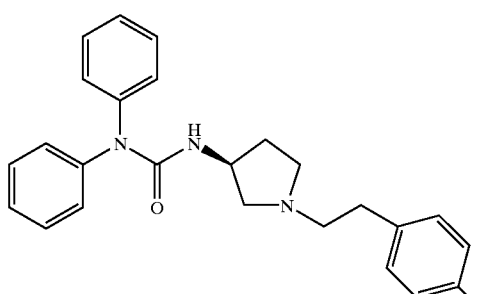
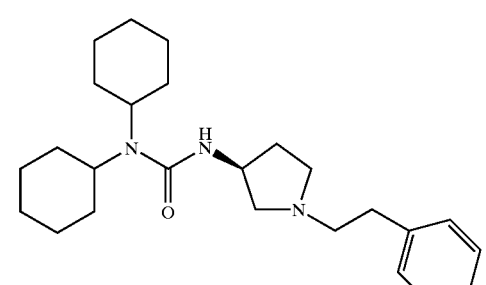
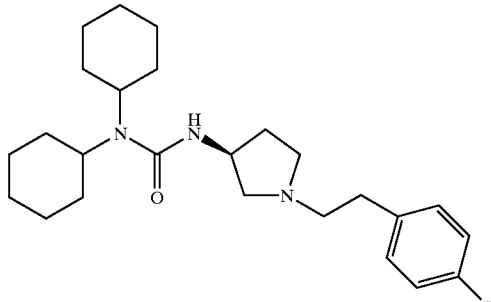

-continued

43
-continued
61
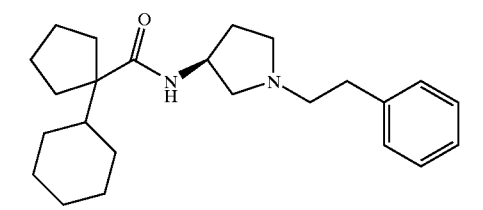
62
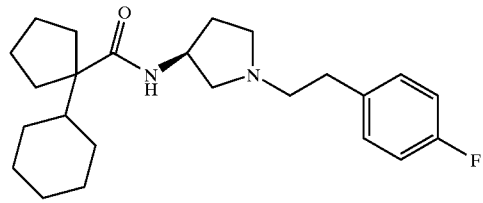
63
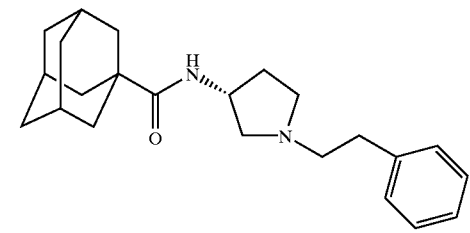
64
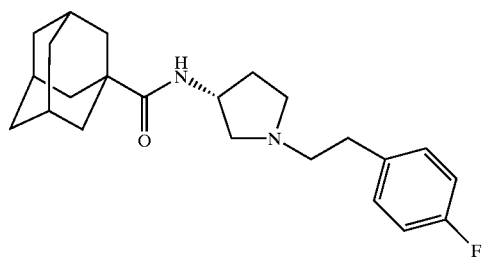
65
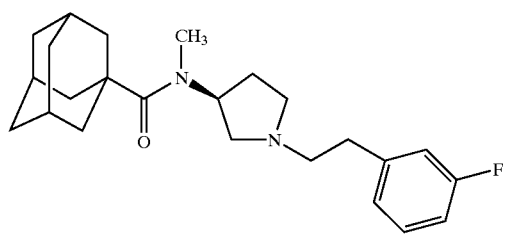
66
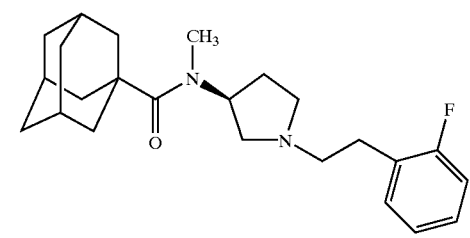
44
-continued
67
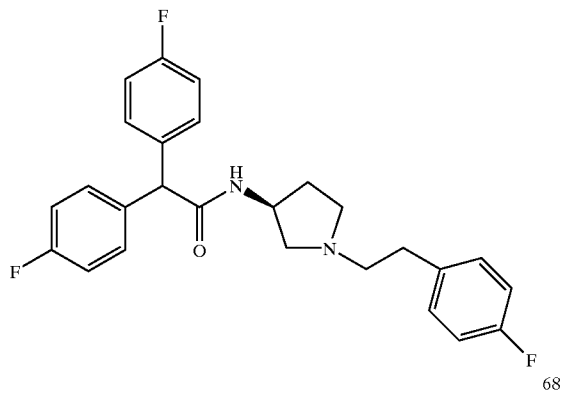
68
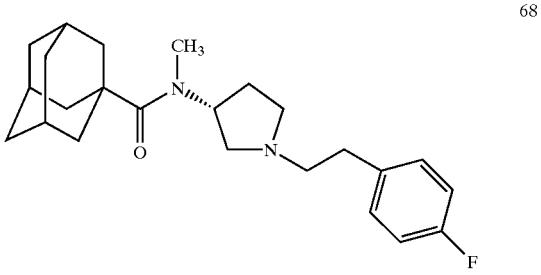
69
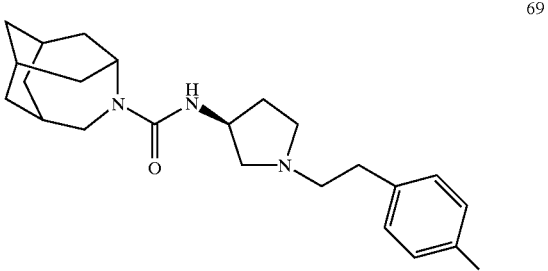
70
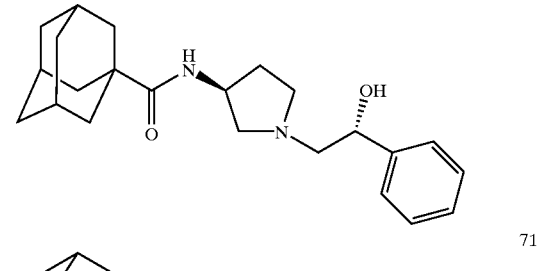
71
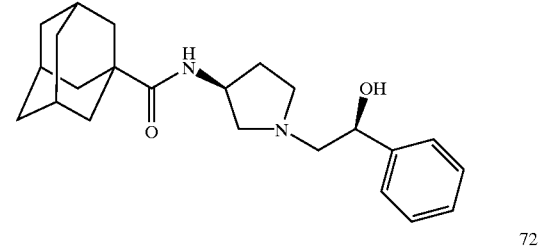
72
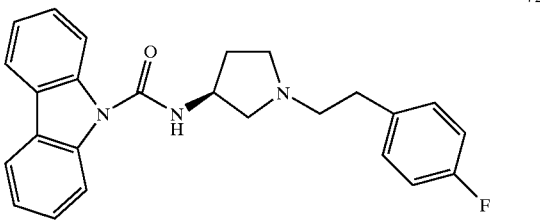

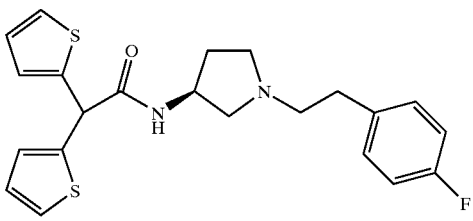

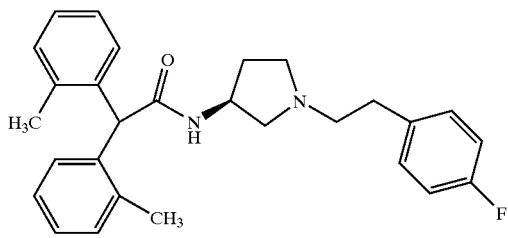

Example 76

1-Adamantanesulfinyl chloride and (S)-3-amino-1-(2-(4-fluorophenyl)ethyl)pyrrolidine were reacted under the same conditions as in Example 53 to give (S)-N-(1-(2-(4-fluorophenyl)ethyl)pyrrolidin-3-yl)-1-adamantanesulfinamide.

Example 77

1-Adamantanesulfonyl chloride and (S)-3-amino-1-(2-(4-fluorophenyl)ethyl)pyrrolidine were reacted under the same conditions as in Example 53 to give (S)-N-(1-(2-(4-fluorophenyl)ethyl)pyrrolidin-3-yl)-1-adamantanesulfonamide.

Example 78

2-Bicyclo[2.2.2]octanecarbonyl chloride and (S)-3-amino-1-(2-(4-fluorophenyl)ethyl)pyrrolidine were reacted under the same conditions as in Example 53 to give (S)-N-(1-(2-(4-fluorophenyl)ethyl)pyrrolidin-3-yl)-2-bicyclo[2.2.2]octanecarboxamide.

Example 79

1-Azabicyclo[2.2.2]octane-3-carbonyl chloride and (S)-3-amino-1-(2-(4-fluorophenyl)ethyl)pyrrolidine were reacted under the same conditions as in Example 53 to give (S)-N-(1-(2-(4-fluorophenyl)ethyl)pyrrolidin-3-yl)-1-azabicyclo[2.2.2]octane-3-carboxamide.

Example 80

1-Azabicyclo[2.2.2]octane-1-oxide-3-carbonyl chloride and (s)-3-amino-1-(2-(4-fluorophenyl)ethyl)pyrrolidine were reacted under the same conditions as in Example 53 to give (S)-N-(1-(2-(4-fluorophenyl)ethyl)pyrrolidin-3-yl)-1-azabicyclo[2.2.2]octane-1-oxide-3-carboxamide.

Example 81

Bicyclo[2.2.2]octane-1-carbonyl chloride and (S)-3-amino-1-(2-(4-fluorophenyl)ethyl)pyrrolidine were reacted under the same conditions as in Example 53 to give (S)-N-(1-(2-(4-fluorophenyl)ethyl)pyrrolidin-3-yl)-bicyclo[2.2.2]octane-1-carboxamide.

Example 82

1-Azabicyclo[2.2.2]octane-4-carbonyl chloride and (S)-3-amino-1-(2-(4-fluorophenyl)ethyl)pyrrolidine were reacted under the same conditions as in Example 53 to give (S)-N-(1-(2-(4-fluorophenyl)ethyl)pyrrolidin-3-yl)-1-azabicyclo[2.2.2]octane-4-carboxamide.

Example 83

1-Azabicyclo[2.2.2]octane-1-oxide-4-carbonyl chloride and (S)-3-amino-1-(2-(4-fluorophenyl)ethyl)pyrrolidine were reacted under the same conditions as in Example 53 to give (S)-N-(1-(2-(4-fluorophenyl)ethyl)pyrrolidin-3-yl)-1-azabicyclo[2.2.2]octane-1-oxide-4-carboxamide.

Example 84

3-Azabicyclo[3.2.1]octane and (S)-3-amino-1-(2-(4-fluorophenyl)ethyl)pyrrolidine were reacted under the same conditions as in Example 69 to give (S)-N-(1-(2-(4-fluorophenyl)ethyl)pyrrolidin-3-yl)-3-azabicyclo[3.2.1]octane-3-carboxamide.

Example 85

8-Azabicyclo[3.2.1]octane and (S)-3-amino-1-(2-(4-fluorophenyl)ethyl)pyrrolidine were reacted under the same conditions as in Example 69 to give (S)-N-(1-(2-(4-fluorophenyl)ethyl)pyrrolidin-3-yl)-8-azabicyclo[3.2.1]octane-8-carboxamide.

Example 86

1-Azaadamantane-4-carbonyl chloride and (S)-3-amino-1-(2-(4-fluorophenyl)ethyl)pyrrolidine were reacted under the same conditions as in Example 53 to give (S)-N-(1-(2-(4-fluorophenyl)ethyl)pyrrolidin-3-yl)-1-azaadamantane-4-carboxamide.

Example 87

1-Azaadamantane-1-oxide-4-carbonyl chloride and (S)-3-amino-1-(2-(4-fluorophenyl)ethyl)pyrrolidine were reacted under the same conditions as in Example 53 to give (S)-N-(1-(2-(4-fluorophenyl)ethyl)pyrrolidin-3-yl)-1-azaadamantane-1-oxide-4-carboxamide.

Example 88

1,4-Diazatricyclo[4.3.1.1(3,8)]undecane and (S)-3-amino-1-(2-(4-fluorophenyl)ethyl)pyrrolidine were reacted under the same conditions as in Example 69 to give (S)-N-(1-(2-(4-fluorophenyl)ethyl)pyrrolidin-3-yl)-1,4-diazatricyclo[4.3.1.1(3,8)]undecane-4-carboxamide.

Example 89

1,4-Diazatricyclo[4.3.1.1(3,8)]undecane-1-oxide and (S)-3-amino-1-(2-(4-fluorophenyl)ethyl)pyrrolidine were reacted under the same conditions as in Example 69 to give (S)-N-(1-(2-(4-fluorophenyl)ethyl)pyrrolidin-3-yl)-1,4-diazatricyclo-[4.3.1.1(3,8)]undecane-1-oxide-4-carboxamide.

Example 90

1-Aza-5-methyladamantane-3-carbonyl chloride and (S)-3-amino-1-(2-(4-fluorophenyl)ethyl)pyrrolidine were reacted under the same conditions as in Example 53 to give (S)-N-(1-(2-(4-fluorophenyl)ethyl)pyrrolidin-3-yl)-1-aza-5-methyladamantane-3-carboxamide.

Example 91

1-Aza-5-methyladamantane-1-oxide-3-carbonyl chloride and (S)-3-amino-1-(2-(4-fluorophenyl)ethyl)pyrrolidine were reacted under the same conditions as in Example 53 to give (S)-N-(1-(2-(4-fluorophenyl)ethyl)pyrrolidin-3-yl)-1-aza-5-methyladamantane-1-oxide-3-carboxamide.

Example 92

2-Azaadamantane and (S)-3-amino-1-(2-(4-fluorophenyl)ethyl)pyrrolidine were reacted under the same conditions as in Example 69 to give (S)-N-(1-(2-(4-fluorophenyl)ethyl)pyrrolidin-3-yl)-2-azaadamantane-2-carboxamide.

Example 93

1,4-Diazabicyclo[3.2.1]octane and (S)-3-amino-1-(2-(4-fluorophenyl)ethyl)pyrrolidine were reacted under the same conditions as in Example 69 to give (S)-N-(1-(2-(4-fluorophenyl)ethyl)pyrrolidin-3-yl)-1,4-diazabicyclo[3.2.1]octane-4-carboxamide.

Example 94

1,4-Diazabicyclo[3.2.1]octane-1-oxide and (S)-3-amino-1-(2-(4-fluorophenyl)ethyl)pyrrolidine were reacted under the same conditions as in Example 69 to give (S)-N-(1-(2-(4-fluorophenyl)ethyl)pyrrolidin-3-yl)-1,4-diazabicyclo[3.2.1]octane-1-oxide-4-carboxamide.

Example 95

4-Methylquinuclidine-3-carbonyl chloride and (S)-3-amino-1-(2-(4-fluorophenyl)ethyl)pyrrolidine were reacted under the same conditions as in Example 53 to give (S)-N-(1-(2-(4-fluorophenyl)ethyl)pyrrolidin-3-yl)-4-methylquinuclidine-3-carboxamide.

Example 96

4-Methylquinuclidine-1-oxide-3-carbonyl chloride and (S)-3-amino-1-(2-(4-fluorophenyl)ethyl)pyrrolidine were reacted under the same conditions as in Example 53 to give (S)-N-(1-(2-(4-fluorophenyl)ethyl)pyrrolidin-3-yl)-4-methylquinuclidine-1-oxide-3-carboxamide.

Example 97

Quinuclidine-2-carbonyl chloride and (S)-3-amino-1-(2-(4-fluorophenyl)ethyl)pyrrolidine were reacted under the same conditions as in Example 53 to give (S)-N-(1-(2-(4-fluorophenyl)ethyl)pyrrolidin-3-yl)-quinuclidine-2-carboxamide.

Example 98

Quinuclidine-1-oxide-2-carbonyl chloride and (S)-3-amino-1-(2-(4-fluorophenyl)ethyl)pyrrolidine were reacted under the same conditions as in Example 53 to give (S)-N-(1-(2-(4-fluorophenyl)ethyl)pyrrolidin-3-yl)-quinuclidine-1-oxide-2-carboxamide.

Example 99

3-Aminoquinuclidine and (S)-3-amino-1-(2-(4-fluorophenyl)ethyl)pyrrolidine were reacted under the same conditions as in Example 69 to give 1-(quinuclidin-3-yl)-3-((S)-1-(2-(4-fluorophenyl)ethyl)pyrrolidin-3-yl)urea.

Example 100

3-Aminoquinuclidine-1-oxide and (S)-3-amino-1-(2-(4-fluorophenyl)ethyl)pyrrolidine were reacted under the same conditions as in Example 69 to give 1-(quinuclidine-1-oxide-3-yl)-3-((S)-1-(2-(4-fluorophenyl)ethyl)pyrrolidin-3-yl)urea.

Example 101

1-Adamantanesulfinyl chloride and (S)-3-amino-1-(2-phenylethyl)pyrrolidine were reacted under the same conditions as in Example 53 to give (S)-N-(1-(2-phenylethyl)pyrrolidin-3-yl)-1-adamantanesulfinamide.

Example 102

1-Adamantanesulfonyl chloride and (S)-3-amino-1-(2-phenylethyl)pyrrolidine were reacted under the same conditions as in Example 53 to give (S)-N-(1-(2-phenylethyl)pyrrolidin-3-yl)-1-adamantanesulfonamide.

Example 103

2-Bicyclo[2.2.2]octanecarbonyl chloride and (S)-3-amino-1-(2-phenylethyl)pyrrolidine were reacted under the same conditions as in Example 53 to give (S)-N-(1-(2-phenylethyl)pyrrolidin-3-yl)-2-bicyclo[2.2.2]octanecarboxamide.

Example 104

1-Azabicyclo[2.2.2]octane-3-carbonyl chloride and (S)-3-amino-1-(2-phenylethyl)pyrrolidine were reacted under the same conditions as in Example 53 to give (S)-N-(1-(2-phenylethyl)pyrrolidin-3-yl)-1-azabicyclo[2.2.2]octane-3-carboxamide.

Example 105

1-Azabicyclo[2.2.2]octane-1-oxide-3-carbonyl chloride and (S)-3-amino-1-(2-phenylethyl)pyrrolidine were reacted under the same conditions as in Example 53 to give (S)-N-(1-(2-phenylethyl)pyrrolidin-3-yl)-1-azabicyclo[2.2.2]octane-1-oxide-3-carboxamide.

Example 106

Bicyclo[2.2.2]octane-1-carbonyl chloride and (S)-3-amino-1-(2-phenylethyl)pyrrolidine were reacted under the same conditions as in Example 53 to give (S)-N-(1-(2-phenylethyl)pyrrolidin-3-yl)bicyclo[2.2.2]octane-1-carboxamide.

Example 107

1-Azabicyclo[2.2.2]octane-4-carbonyl chloride and (S)-3-amino-1-(2-phenylethyl)pyrrolidine were reacted under the same conditions as in Example 53 to give (S)-N-(1-(2-phenylethyl)pyrrolidin-3-yl)-1-azabicyclo[2.2.2]octane-4-carboxamide.

Example 108

1-Azabicyclo[2.2.2]octane-1-oxide-4-carbonyl chloride and (S)-3-amino-1-(2-phenylethyl)pyrrolidine were reacted under the same conditions as in Example 53 to give (S)-N-(1-(2-phenylethyl)pyrrolidin-3-yl)-1-azabicyclo[2.2.2]octane-1-oxide-4-carboxamide.

Example 109

3-Azabicyclo[3.2.1]octane and (S)-3-amino-1-(2-phenylethyl)pyrrolidine were reacted under the same conditions as in Example 69 to give (S)-N-(1-(2-phenylethyl)pyrrolidin-3-yl)-3-azabicyclo[3.2.]octane-3-carboxamide.

Example 110

8-Azabicyclo[3.2.1]octane and (S)-3-amino-1-(2-phenylethyl)pyrrolidine were reacted under the same conditions as in Example 69 to give (S)-N-(1-(2-phenylethyl)pyrrolidin-3-yl)-8-azabicyclo[3.2.1]octane-8-carboxamide.

Example 111

1-Azaadamantane-4-carbonyl chloride and (S)-3-amino-1-(2-phenylethyl)pyrrolidine were reacted under the same conditions as in Example 53 to give (S)-N-(1-(2-phenylethyl)pyrrolidin-3-yl)-1-azaadamantane-4-carboxamide.

Example 112

1-Azaadamantane-1-oxide-4-carbonyl chloride and (S)-3-amino-1-(2-phenylethyl)pyrrolidine were reacted under the same conditions as in Example 53 to give (S)-N-(1-(2-phenylethyl)pyrrolidin-3-yl)-1-azaadamantane-1-oxide-4-carboxamide.

Example 113

1,4-Diazatricyclo[4.3.1.1(3,8)]undecane and (S)-3-amino-1-(2-phenylethyl)pyrrolidine were reacted under the same conditions as in Example 69 to give (S)-N-(1-(2-phenylethyl)pyrrolidin-3-yl)-1,4-diazatricyclo[4.3.1.1(3,8)]undecane-4-carboxamide.

Example 114

1,4-Diazatricyclo[4.3.1.1(3,8)]undecane-1-oxide and (S)-3-amino-1-(2-phenylethyl)pyrrolidine were reacted under the same conditions as in Example 69 to give (S)-N-(1-(2-phenylethyl)pyrrolidin-3-yl)-1,4-diazatricyclo[4.3.1.1(3,8)]undecane-1-oxide-4-carboxamide.

Example 115

1-Aza-5-methyladamantane-3-carbonyl chloride and (S)-3-amino-1-(2-phenylethyl)pyrrolidine were reacted under the same conditions as in Example 53 to give (S)-N-(1-(2-phenylethyl)pyrrolidin-3-yl)-1-aza-5-methyladamantane-3-carboxamide.

Example 116

1-Aza-5-methyladamantane-1-oxide-3-carbonyl chloride and (s)-3-amino-1-(2-phenylethyl)pyrrolidine were reacted under the same conditions as in Example 53 to give (S)-N-(1-(2-phenylethyl)pyrrolidin-3-yl)-1-aza-5-methyladamantane-1-oxide-3-carboxamide.

Example 117

2-Azaadamantane and (S)-3-amino-1-(2-phenylethyl)pyrrolidine were reacted under the same conditions as in Example 69 to give (S)-N-(1-(2-phenylethyl)pyrrolidin-3-yl)-2-azaadamantane-2-carboxamide.

Example 118

1,4-Diazabicyclo[3.2.1]octane and (S)-3-amino-1-(2-phenylethyl)pyrrolidine were reacted under the same conditions as in Example 69 to give (S)-N-(1-(2-phenylethyl)pyrrolidin-3-yl)-1,4-diazabicyclo[3.2.1]octane-4-carboxamide.

Example 119

1,4-Diazabicyclo[3.2.1]octane-1-oxide and (S)-3-amino-1-(2-phenylethyl)pyrrolidine were reacted under the same conditions as in Example 69 to give (S)-N-(1-(2-phenylethyl)pyrrolidin-3-yl)-1,4-diazabicyclo[3.2.1]octane-1-oxide-4-carboxamide.

Example 120

4-Methylquinuclidine-3-carbonyl chloride and (S)-3-amino-1-(2-phenylethyl)pyrrolidine were reacted under the same conditions as in Example 53 to give (S)-N-(1-(2-phenylethyl)pyrrolidin-3-yl)-4-methylquinuclidine-3-carboxamide.

Example 121

4-Methylquinuclidine-1-oxide-3-carbonyl chloride and (S)-3-amino-1-(2-phenylethyl)pyrrolidine were reacted under the same conditions as in Example 53 to give (S)-N-(1-(2-phenylethyl)pyrrolidin-3-yl)-4-methylquinuclidine-1-oxide-3-carboxamide.

Example 122

Quinuclidine-2-carbonyl chloride and (S)-3-amino-1-(2-phenylethyl)pyrrolidine were reacted under the same conditions as in Example 53 to give (S)-N-(1-(2-phenylethyl)pyrrolidin-3-yl)quinuclidine-2-carboxamide.

Example 123

Quinuclidine-1-oxide-2-carbonyl chloride and (S)-3-amino-1-(2-phenylethyl)pyrrolidine were reacted under the same conditions as in Example 53 to give (S)-N-(1-(2-phenylethyl)pyrrolidin-3-yl)-quinuclidine-1-oxide-2-carboxamide.

Example 124

3-Aminoquinuclidine and (S)-3-amino-1-(2-phenylethyl)pyrrolidine were reacted under the same conditions as in Example 69 to give 1-(quinuclidin-3-yl)-3-((S)-1-(2-phenylethyl)pyrrolidin-3-yl)urea.

Example 125

3-Aminoquinuclidine-1-oxide and (S)-3-amino-1-(2-phenylethyl)pyrrolidine were reacted under the same conditions as in Example 69 to give 1-(quinuclidin-1-oxide-3-yl)-3-((S)-1-(2-phenylethyl)pyrrolidin-3-yl)urea.

The formulas of the compounds obtained in the above-mentioned Examples 76–125 are as follows.

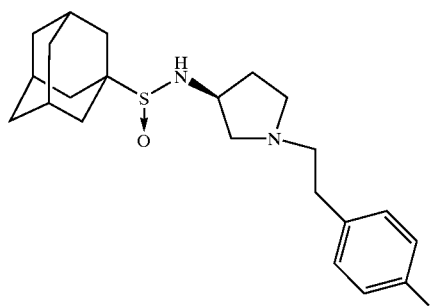
76
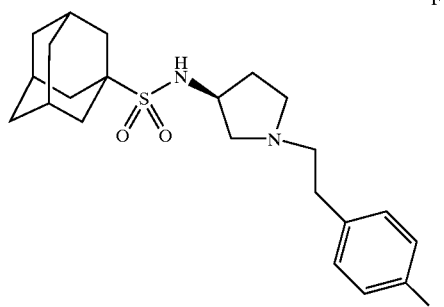
77
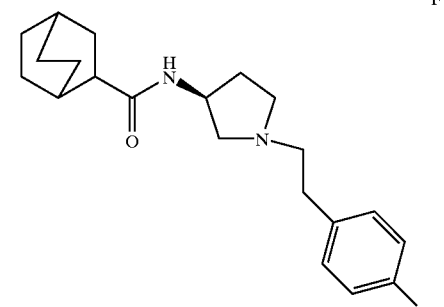
78
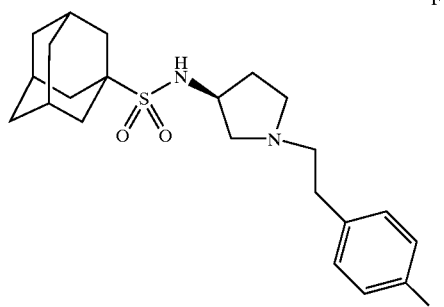
79
80
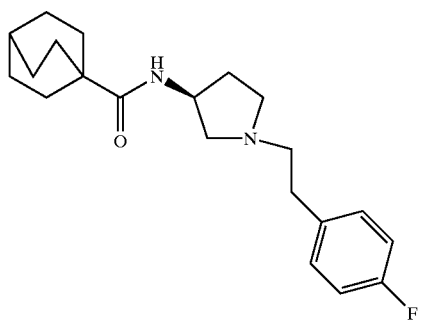
81
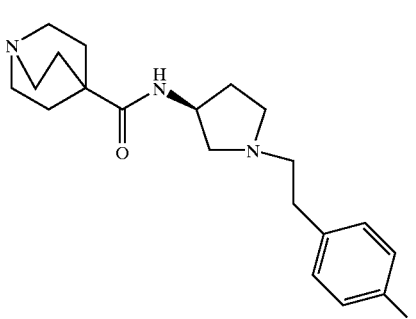
82
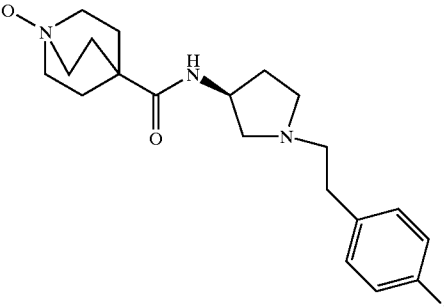
83
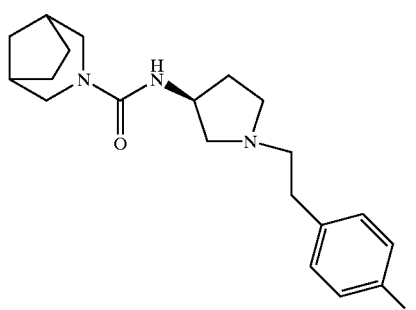
84
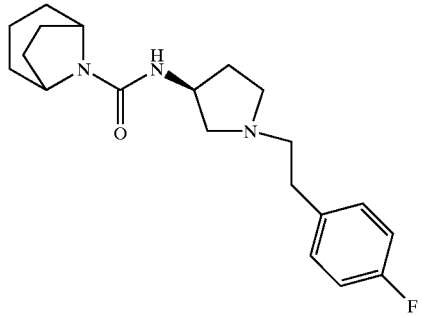
85

86 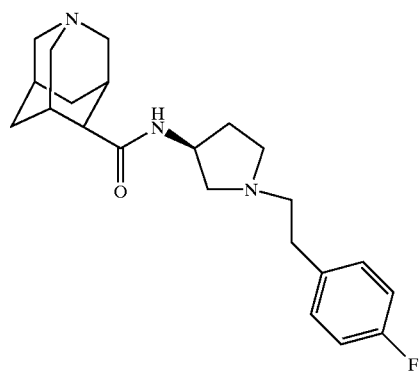
87 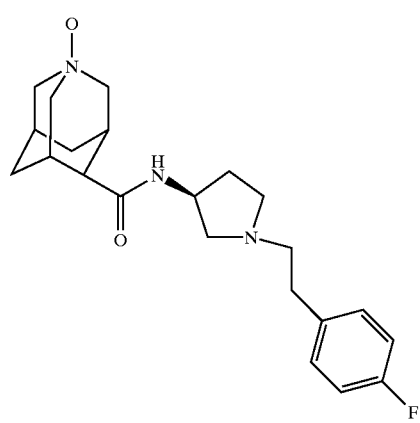
88 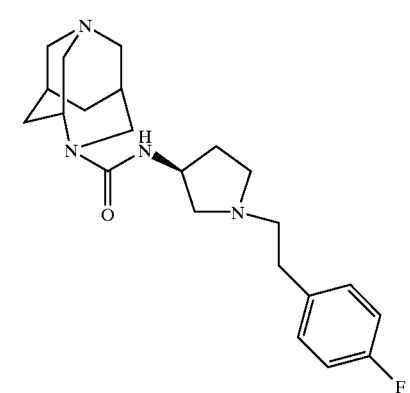
89 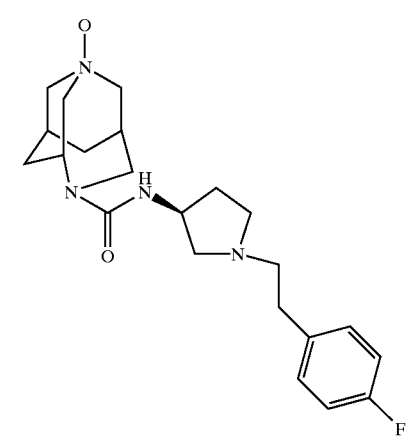
90 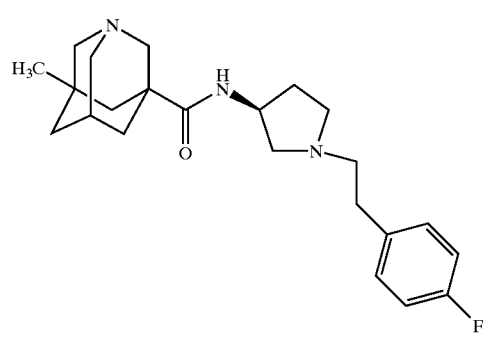
91 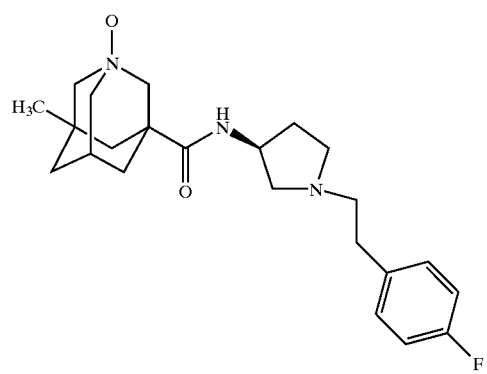
92 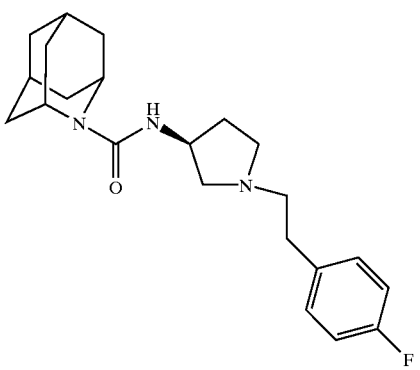
93 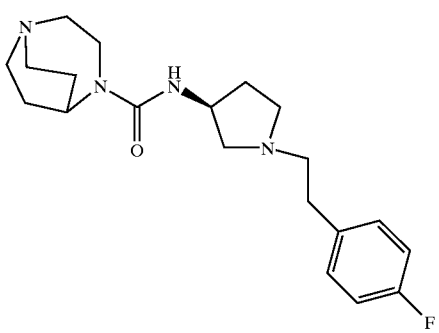

94
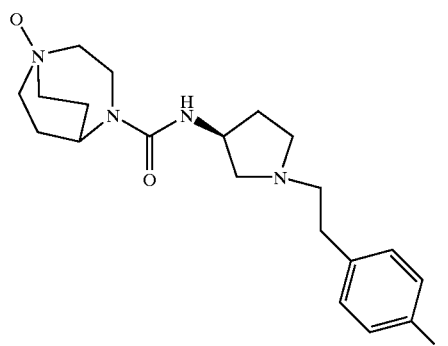
95
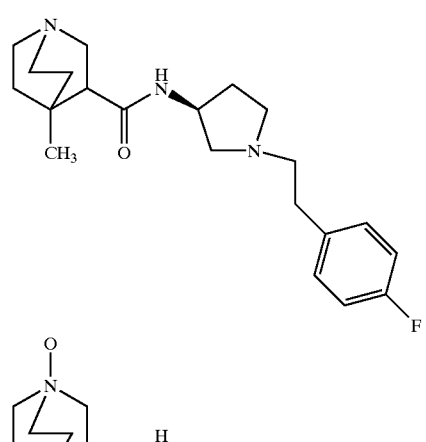
96
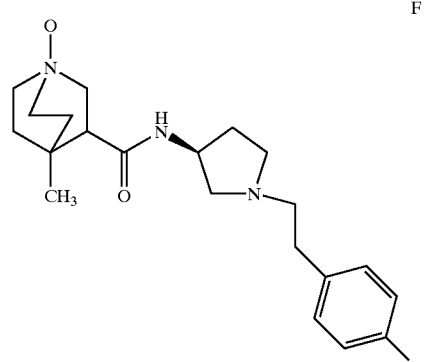
97
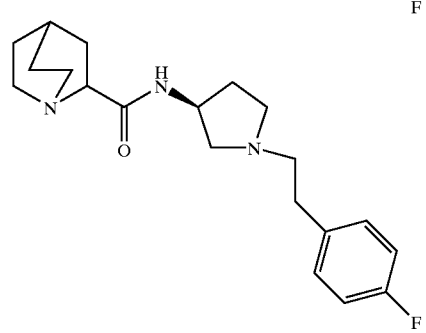
98
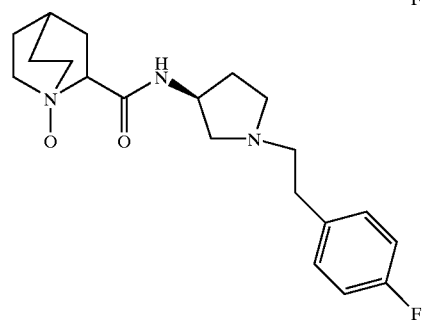
99
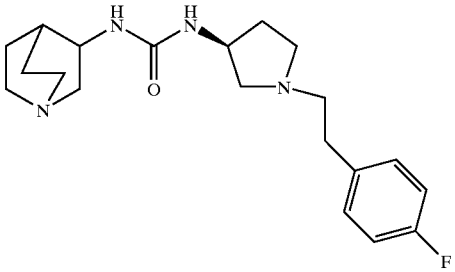
100
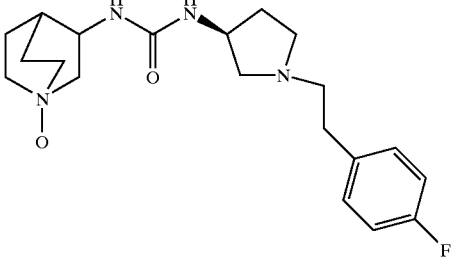
101
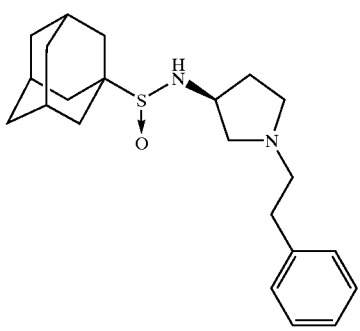
102
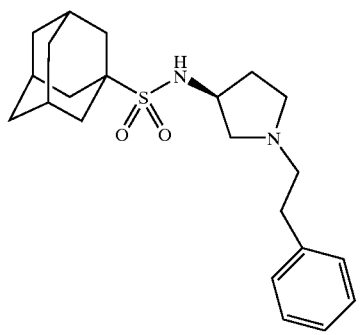
103
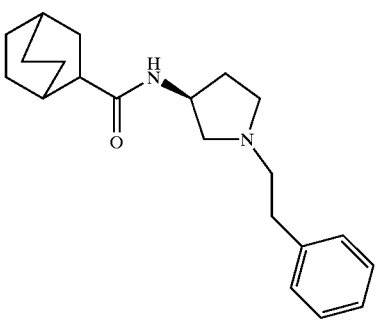

104
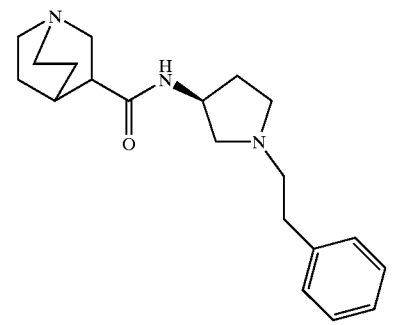
105
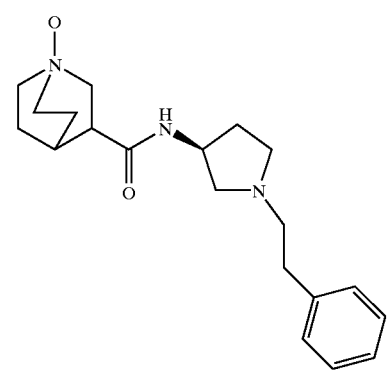
106
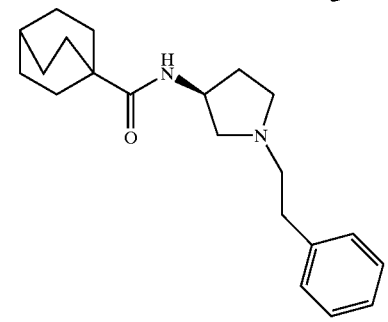
107
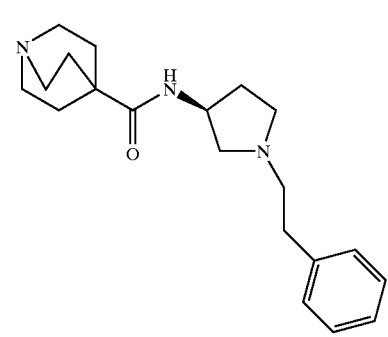
108
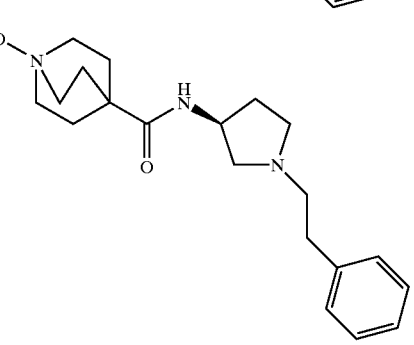
109
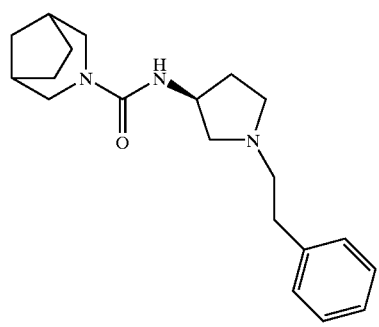
110
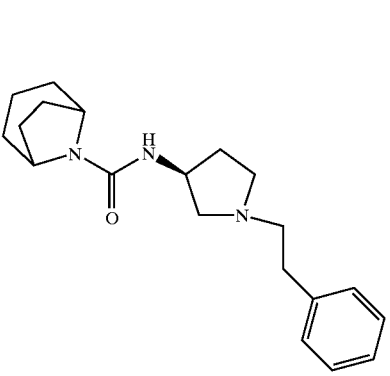
111
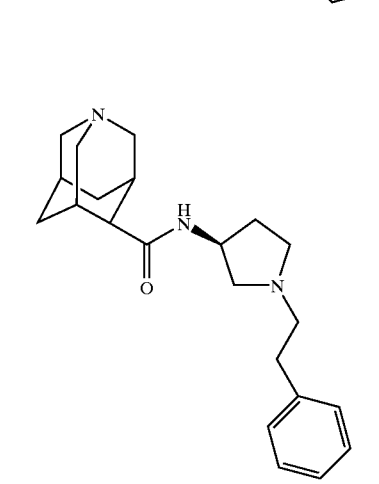
112
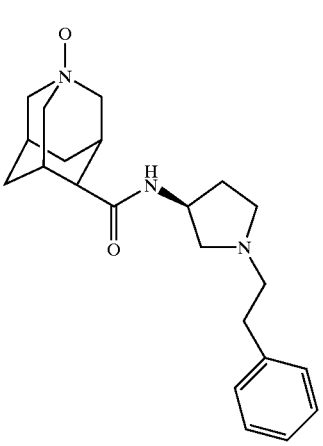

113 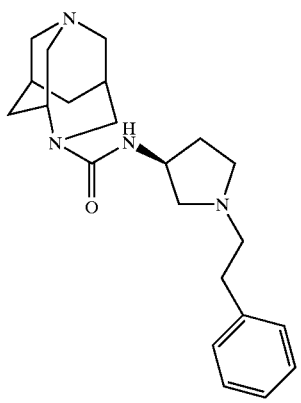
114 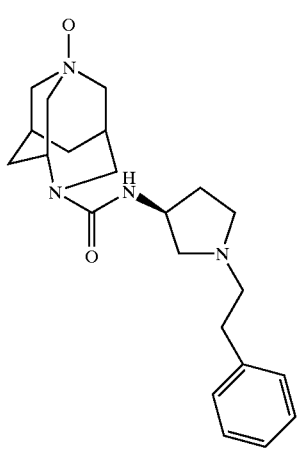
115 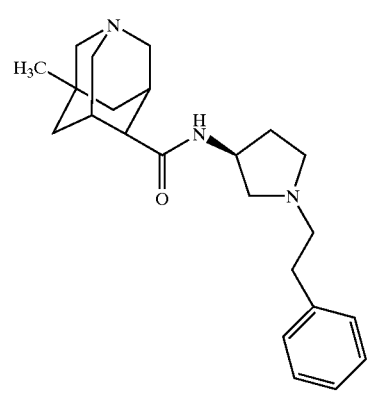
116 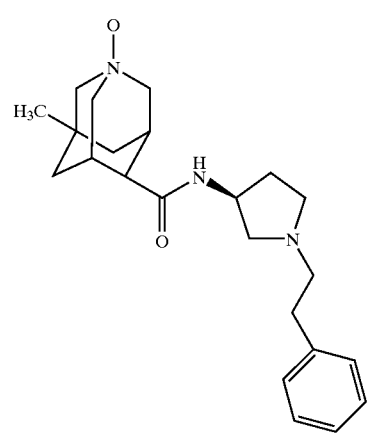
117 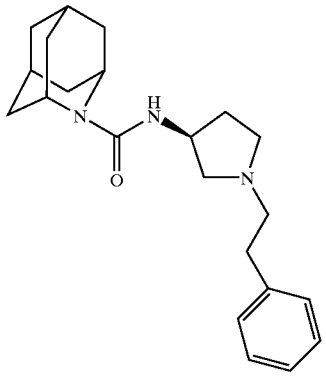
118 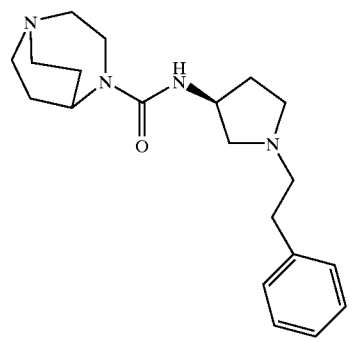
119 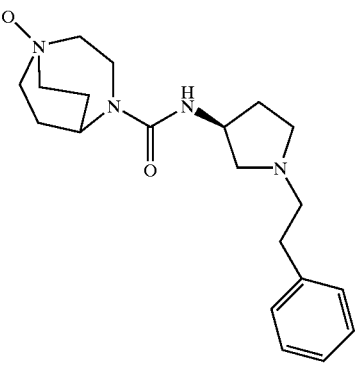
120 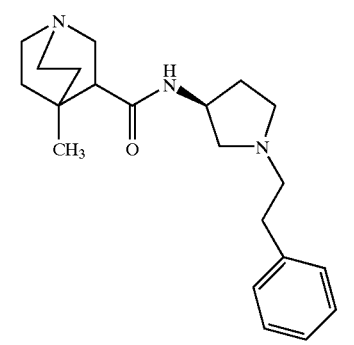

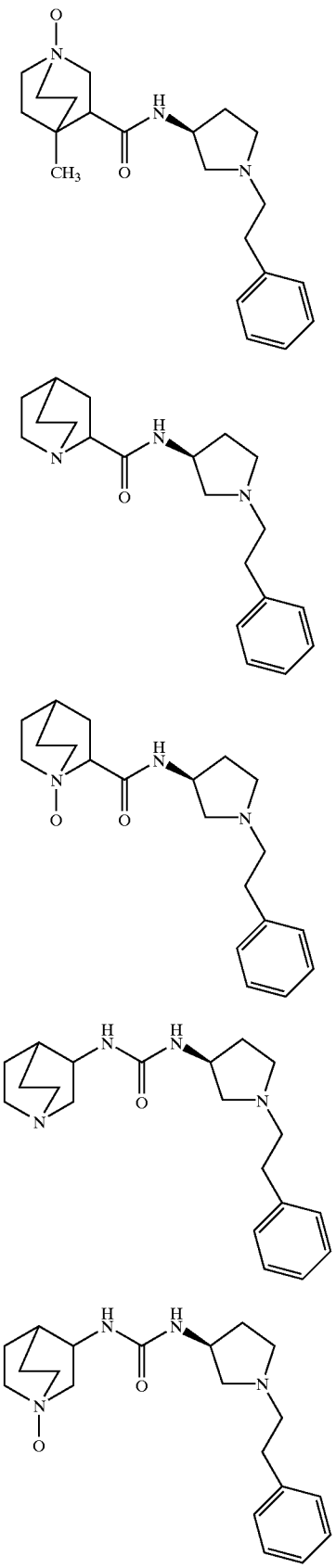

Formulation Example 1

A compound of Example 2 (0.5 part), lactose (25 parts), crystalline cellulose (35 parts) and corn starch (3 parts) were thoroughly admixed and kneaded well with a binder made from corn starch (2 parts). The kneaded product was passed through a 16 mesh sieve, dried in an oven at 50° C. and passed through a 24 mesh sieve. The kneaded powder thus obtained, corn starch (8 parts), crystalline cellulose (11 parts) and talc (9 parts) were thoroughly admixed and compressed with a punch into tablets each containing 0.5 mg of the active ingredient.

Formulation Example 2

A compound (1.0 mg) of Example 2 and sodium chloride (9.0 mg) were dissolved in injectable water, and the solution was filtered to remove pyrogen. The filtrate was aseptically filled in ampoules, which were sterilized and melt-sealed to give an injection containing 1.0 mg of the active ingredient.

The superior pharmacological activity of the compound of the formula (I) can be established by the following series of tests.

Experimental Example 1

Affinity for 5-HT$_2$ Receptor (Binding with $^3$H-ketanserine)

Preparation of a crude synapse membrane and a binding test were performed according to the method of Leysen J. E. et al. [Molecular Pharmacology, Vol. 21, p. 301 (1982)]. A crude synapse membrane was prepared from a freeze-dried rat cerebral cortex, and the membrane specimen and $^3$H-ketanserine were incubated in the presence of a test compound at 37° C. for 20 min. After the completion of the reaction, the reaction mixture was immediately filtered by suction on a Whatmann GF/B filter (trademark), and the radioactivity on the filter was measured on a liquid scintillation counter. The amount of non-specific binding was measured in the presence of 10 μM mianserin. The 50% inhibition concentration (IC$_{50}$) of the test compound was calculated by the nonlinear regression. In the same manner as above, a comparative test was performed using sarpogrelate as a control compound. The results are shown in Table 1.

Experimental Example 2

Platelet Aggregation Suppressive Action

Preparation of platelet rich plasma and a platelet aggregation test were performed according to the method of Born, G. V. R. et al. [Journal of Physiology, Vol. 168, p. 178 (1963)] as in the following. Blood was drawn from the carotid of male Japanese white rabbit with local anesthesia with xylocaine, using a syringe previously added with 3.8% sodium citrate in a 1/10 amount of the blood. This blood was centrifuged at 1000 round/min for 10 min at room temperature to give a platelet rich plasma (PRP) supernatant. This supernatant was further centrifuged at 3000 round/min for 10 min to give a platelet poor plasma (PPP) supernatant. Taking the measurement values of PRP and PPP as 0% aggregation and 100% aggregation, respectively, the platelet aggregation rate (%) was calculated. A test compound (3 μl) was added to 300 μl of PRP and the mixture was incubated at 37° C. for 5 min. Thereto were added, as aggregation inducing substances, collagen at a concentration prohibitive on aggregation by its single administration, and the final concentration of 3 μM of 5-HT, and the aggregation reaction was recorded for 7 min. The effect of the test compound was determined as percent suppression relative to the control group, using the maximum aggregation as an index. The 50% inhibition concentration ($IC_{50}$) of the test compound was calculated by the nonlinear regression. In the same manner as above, a comparative experiment was conducted for the use of sarpogrelate and cilostazol, respectively as a control compound.

The results are shown in Table 1.

TABLE 1

| compound | Experimental Example 1<br>5-$HT_2$ binding $IC_{50}$ (nM) | Experimental Example 2<br>platelet aggregation<br>suppressive action $IC_{50}$ (nM) |
|---|---|---|
| Example 2 | 0.18 | 1.9 |
| Sarpogrelate | 27 | 260 |
| Cilostazol | NT | 1378 |

NT; Not Tested

Experimental Example 3

Effect on Rat Intermittent Claudication Model

Rat was anesthetized and the right thigh was opened to expose femoral artery, which was ligated with a silk thread at a position nearest possible to the heart (upstream). In addition, a position about 1 cm from the ligation site to the periphery was ligated with a silk thread, making two ligature sites. Starting from the next day of preparation of a model to day 8 therefrom, a drug was orally administered twice a day for 8 days. However, the drug was orally administered only in the evening of the first day of administration and only in the morning of the final administration day. The walking distance was measured one day before model preparation (initial value), day 1, day 5 and day 8 with a treadmill apparatus. Using a gait test table without an angle of inclination, the conveyor advance speed was first set to 15 m/min, and the speed was increased every 5 min by 5 m/min until the animal failed walking three times, based on which the walking distance of the rat was measured. In the same manner as above, a comparative experiment was performed using sarpogrelate and cilostazol, respectively as a control compound.

The results are shown in Table 2. In the Table, the values are mean±standard error (n=8 but n=6 only for sarpogrelate group).

TABLE 2

| drug group | Value (m)<br>before<br>ligation | before drug<br>administration<br>(Δm) | 8 days after<br>administration<br>(Δm) |
|---|---|---|---|
| Vehicle | 326.6 ± 16.9 | −211.5 ± 14.9 | −192.0 ± 23.9 |
| Example 2 (3 mg/kg) | 329.0 ± 20.7 | −212.0 ± 18.3 | −94.3 ± 36.1 * |
| Example 2 (10 mg/kg) | 328.9 ± 25.0 | −214.8 ± 22.5 | −89.9 ± 22.2 * |
| Example 2 (30 mg/kg) | 318.0 ± 31.9 | −210.4 ± 24.1 | −88.6 ± 25.0 * |
| Sarpogrelate (100 mg/kg) | 325.7 ± 33.4 | −217.2 ± 26.7 | −151.3 ± 35.4 |
| Cilostazol (100 mg/kg) | 322.4 ± 27.5 | −221.4 ± 24.6 | −149.8 ± 22.7 |

*$p < 0.05$ vs vehicle (Dunnett's method)

In the vehicle group, the walking distance decreased from 326.6±16.9 m to 115.1±6.1 m, due to the femoral artery ligation, and no recovery was observed in 8 days. In the case of compound of Example 2 (3 mg/kg, 10 mg/kg and 30 mg/kg, b.i.d.), the walking distance significantly increased at day 8 of ligation. In contrast, sarpogrelate and cilostazol increased the walking distance but the increase was not significant.

Experimental Example 4

Effect on Lauric Acid-induced Peripheral Arterial Obstruction Model (Preventive Effect)

Under anesthesia, lauric acid (0.75 mg/0.15 mL) was injected into the right femoral artery of Wistar rats (6–8 weeks of age). A drug was administered 1 hour before the lauric acid injection. The drug was orally administered twice a day for 8 days. In the same manner as above, a comparative experiment was performed using cilostazol as a control compound.

The results are shown in Table 3. In the Table, the values are mean±standard error (n=12).

TABLE 3

| | Lesion score | | | |
|---|---|---|---|---|
| drug group | 1 day<br>later | 3 days<br>later | 5 days<br>later | 7 days<br>later |
| Vehicle | 3.3 ± 0.2 | 4.5 ± 0.2 | 5.0 ± 0.3 | 5.0 ± 0.3 |
| Example 2<br>(10 mg/kg) | 1.8 ± 0.1 ** | 2.1 ± 0.2 ** | 1.8 ± 0.3 ** | 1.9 ± 0.5 ** |
| Example 2<br>(30 mg/kg) | 1.8 ± 0.2 ** | 2.0 ± 0.3 ** | 1.5 ± 0.4 ** | 1.2 ± 0.5 ** |
| Cilostazol<br>(100 mg/kg) | 1.8 ± 0.1 ** | 2.2 ± 0.2 ** | 1.8 ± 0.4 ** | 2.2 ± 0.5 ** |

**$p < 0.01$ vs vehicle (Dunnett's method)
<lesion score>
0: normal
1: slight edema
2: serious edema
3: necrosis, mummification or deciduation of the nail
4: necrosis, mummification or deciduation of the toe
5: necrosis, mummification or deciduation of the half area of the hind paw
6: necrosis, mummification or deciduation of the hind paw In the lauric acid-induced peripheral arterial obstruction model, administration of compound of Example 2 (10 mg/kg and 30 mg/kg) and cilostazol (100 mg/kg) prior to the lauric acid injection significantly reduced the peripheral circulatory disturbance.

Experimental Example 5

Effect on Rat Lauric Acid-induced Peripheral Arterial Obstruction Model (Therapeutic Effect)

Under anesthesia, lauric acid (0.75 mg/0.15 mL) was injected into the right femoral artery of Wistar rats (6–8 weeks of age). A drug was administered one day after the lauric acid injection. The drug was orally administered twice a day for 7 days. In the same manner as above, a comparative experiment was performed using sarpogrelate and cilostazol as a control compound.

The results are shown in Table 4. In the Table, the values are mean±standard error (n=11).

TABLE 4

| | Lesion score | | | |
|---|---|---|---|---|
| drug group | 1 day<br>later | 3 days<br>later | 5 days<br>later | 7 days<br>later |
| Vehicle | 2.1 ± 0.2 | 3.0 ± 0.3 | 3.4 ± 0.4 | 3.6 ± 0.5 |
| Example 2<br>(10 mg/kg) | 2.0 ± 0.0 | 2.2 ± 0.1 | 2.2 ± 0.4 | 2.2 ± 0.4 |
| Example 2<br>(30 mg/kg) | 1.8 ± 0.1 | 1.7 ± 0.2 ** | 1.3 ± 0.3 ** | 0.9 ± 0.5 ** |
| Sarpogrelate<br>(100 mg/kg) | 1.9 ± 0.2 | 2.3 ± 0.3 | 2.1 ± 0.5 | 2.4 ± 0.6 |

TABLE 4-continued

| drug group | Lesion score | | | |
|---|---|---|---|---|
| | 1 day later | 3 days later | 5 days later | 7 days later |
| Cilostazol (100 mg/kg) | 1 6 ± 0.2 | 1.5 ± 0.3 ** | 1.4 ± 0.4 ** | 1.3 ± 0.4 ** |

**p < 0.01 vs vehicle (Dunnett's method)
<lesion score>
0: normal
1: slight edema
2: serious edema
3: necrosis, mummification or deciduation of the nail
4: necrosis, mummification or deciduation of the toe
5: necrosis, mummification or deciduation of the half area of the hind paw
6: necrosis, mummification or deciduation of the hind paw In the lauric acid-induced peripheral arterial obstruction model, the administration of compound of Example 2 (30 mg/kg) and cilostazol (100 mg/kg) from one day after the lauric acid injection significantly reduced the peripheral circulatory disturbance.

Experimental Example 6

Improvement Effect of Erythrocyte Deformation

Blood was drawn under anesthesia from SHRSP (stroke prone spontaneously hypertensive rat) loaded with 1% saline for 3 weeks, and the time necessary for 0.5 mL of blood to pass through a filter (pore size 5 $\mu$m, Nuclepore) was measured by the Nuclepore membrane filter method of Reid et al., based on which the volume (mL/min) of the erythrocytes passed was calculated. The volume of the erythrocytes passed was taken as an index of erythrocyte deformation. A drug was orally administered 1 hour before drawing the blood. In the same manner as above, a comparative experiment was performed using sarpogrelate as a control compound.

The results are shown in Table 5. In the Table, the values are mean±standard error (n=6).

TABLE 5

| compound | Volume of erythrocytes passed (mL/min) |
|---|---|
| Vehicle | 0.79 ± 0.08 |
| Example 2 (10 mg/kg) | 1.05 ± 0.13 |
| Example 2 (30 mg/kg) | 1.47 ± 0.19 ** |
| Sarpogrelate (100 mg/kg) | 1.01 ± 0.10 |
| Wistar rat (Vehicle) | 1.28 ± 0.09 * |

*p < 0.05,
**p < 0.01 vs vehicle (Dunnett's method)

In SHRSP, the volume of the erythrocyte passed in the compound of Example 2 (10 mg/kg and 30 mg/kg) administration group was 133% and 186% of the vehicle group, and the administration of the compound of Example 2 in 30 mg/kg significantly increased the volume. In contrast, the administration of sarpogrelate (100 mg/kg) increased the volume of erythrocytes passed to 128% of the vehicle group, but this increase was not significant.

Experimental Example 7

Promotion of Collateral Circulation

A collateral circulation model was prepared by rat femoral artery ligation, and a test drug was orally administered 7 days later. At 1 hour from the test drug administration, ADP-added platelet suspension (200 $\mu$M) was administered under anesthesia into the femoral artery (1 mL/kg), and changes in the leg blood flow were measured. In the same manner as above, a comparative experiment was performed using cilostazol as a control compound.

The results are shown in Table 6. In the Table, the values are mean±standard error (n=6).

TABLE 6

| | Change in blood flow (%) | |
|---|---|---|
| drug group | control side | femoral artery ligation side |
| Vehicle | −62.2 ± 2.0 | −70.9 ± 2.0 |
| Example 2 (10 mg/kg) | −10.1 ± 1.4 ** | −11.8 ± 1.2 ** |
| Cilostazol (100 mg/kg) | −27.0 ± 5.0 ** | −63.3 ± 2.4 * |

*p < 0.05,
**p < 0.01 vs vehicle (Dunnett's method)

By the intraarterial injection of ADP-added platelet suspension, the blood flow of the leg on the control side and femoral artery ligation side decreased. The oral administration of the compound of Example 2 (10 mg/kg) suppressed the decrease in the blood flow in the legs on both sides, which decrease being caused by the ADP-added platelet suspension. In contrast, cilostazol (100 mg/kg) suppressed a decrease in the blood flow on the ligation side only slightly. The compound of Example 2 suppressed, unlike cilostazol, a decrease in the blood flow of the leg on the femoral artery ligation side where the collateral circulation is developed, which decrease was caused by the ADP-added platelet suspension.

Experimental Example 8

Effect on Heart Rate and Blood Pressure

A catheter was placed in the femoral artery of Wistar rat, and the blood pressure and heart rate were invasively monitored under no anesthesia or restriction. At 1 hour from the oral administration of the test drug, blood pressure and heart rate were taken. In the same manner as above, a comparative experiment was performed using cilostazol as a control compound.

The results are shown in Table 7. In the Table, the values are mean±standard error (n=4).

TABLE 7

| | blood pressure (mmHg) | | heart rate (beats/min) | |
|---|---|---|---|---|
| drug group | Value before administration | Change of blood pressure | Value before administration | Change of heart rate |
| Vehicle | 120.0 ± 1.8 | 0.5 ± 0.6 | 367.3 ± 14.2 | 14.5 ± 7.8 |
| Example 2 (30 mg/kg) | 120.8 ± 2.2 | 0.0 ± 1.5 | 361.5 ± 7.2 | −1.3 ± 4.7 |
| Example 2 (100 mg/kg) | 119.5 ± 4.7 | −2.8 ± 0.8 | 364.8 ± 19.7 | −4.5 ± 5.2 |
| Cilostazol (100 mg/kg) | 118.5 ± 2.3 | 1.3 ± 1.3 | 368.0 ± 8.2 | 43.8 ± 6.7* |

**p < 0.05 vs vehicle (Dunnett's method)

While compound of Example 2 (30 mg/kg and 100 mg/kg) did not influence the heart rate or blood pressure, cilostazol (300 mg/kg) increased the heart rate.

The compound of the formula (I) of the present invention, an optically active compound thereof and a pharmaceutically acceptable salt thereof have a strong and selective 5-HT$_2$ receptor antagonistic action along with a platelet aggregation suppressive action, a peripheral circulation improving action and a lacrimation promoting action. Furthermore, the compound of the present invention improves erythrocyte deformation and promotes collateral circulation. On the other hand, it shows a small effect on the heart rate and blood pressure, demonstrating very small effect on the heart. Thus, the compound of the present invention is useful as a therapeutic agent for thrombotic embolism, chronic arterial obstruction, intermittent claudication, coronary artery disease, cerebrovascular disorder, peripheral circulatory disturbance, migraine, diabetic peripheral neuropathy, postherpetic neuralgia, glaucoma, dry eye, xerophthalmia, keratitis sicca and the like, with less side effects such as an action on the central nervous system and blood pressure lowering action.

This application is based on application No. 311868/1998 filed in Japan, the contents of which are incorporated hereinto by reference.

What is claimed is:
1. A pyrrolidine compound of the formula (I)

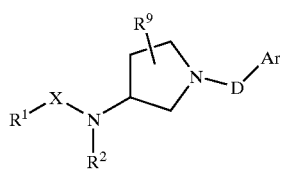

(I)

wherein
$R^1$ is a group selected from the groups of the following formulas (1), (2), (3), (4), (5), (6), (7) and (8)

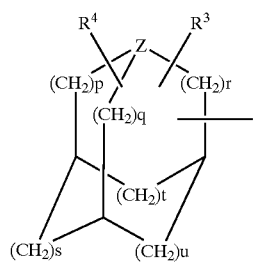

(1)

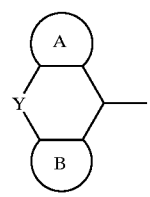

(2)

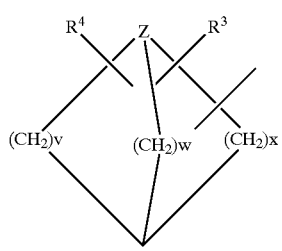

(3)

-continued

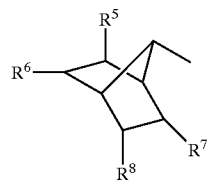

(4)

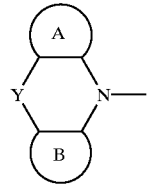

(5)

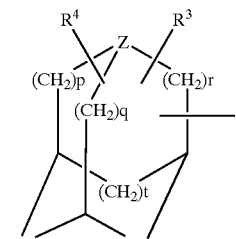

(6)

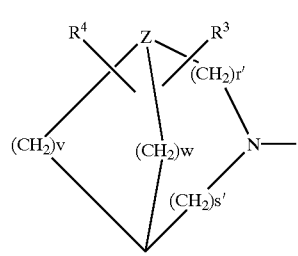

(7)

(8)

wherein
$R^3$ and $R^4$ are the same or different and each is hydrogen, halogen, alkyl, alkoxy, haloalkyl, hydroxy, amino, dialkylamino, nitro, cyano, amido, or $R^3$ and $R^4$ in combination form carbonyl, $R^5$, $R^6$, $R^7$ and $R^8$ are the same or different and each is hydrogen or alkyl, or $R^5$–$R^6$ and $R^7$–$R^8$ are the same or different and each is bonded to form, together with the bond between the carbon atoms they are bonded to, a double bond, optionally substituted cycloalkyl having 3 to 8 carbon atoms, optionally substituted cycloalkenyl having 3 to 8 carbon atoms, optionally substituted cycloalkadienyl having 5 to 8 carbon atoms, optionally substituted aromatic ring or optionally substituted aromatic heterocycle having at least one atom selected from oxygen atom, nitrogen atom and sulfur atom as a heteroatom,
ring A and ring B are the same or different and each is optionally substituted cycloalkyl having 3 to 8 carbon atoms, optionally substituted cycloalkenyl having 3 to 8 carbon atoms, optionally substituted cycloalkadienyl having 5 to 8 carbon atoms, optionally substituted aromatic ring or an optionally substituted aromatic heterocycle having at least one atom selected from oxygen atom, nitrogen atom and sulfur atom as a heteroatom, ring H is optionally substituted cycloalkyl having 3 to 8 carbon atoms, E is optionally substituted cycloalkyl having 3 to 8 carbon atoms, Z is carbon atom, nitrogen atom or N-oxide, Y is not present to make the ring A and ring B independent, or Y is a single bond, oxygen atom, sulfur atom, SO, $SO_2$, $CH_2$, $CH_2CH_2$ or CH=CH, p, q, r, s, t and u are the same or different and each is an integer of 1 or 2, u' is an integer of 0–2, r' and s' are the same or different and each is an integer of 0–3, and v, w and x are the same or different and each is an integer of 1–3, $R^9$ is hydrogen, alkyl having 1 to 6 carbon atoms, alkoxy having 1 to 6 carbon atoms or hydroxyalkyl having 1 to 6 carbon atoms, X is C=O, C=S, NH—C=O, SO or $SO_2$, $R^2$ is hydrogen, alkyl, acyl, optionally substituted arylalkyl, optionally substituted aromatic ring, or an optionally substituted aromatic heterocycle having at least one atom selected from oxygen atom, nitrogen atom and sulfur atom as a heteroatom, D is optionally substituted linear or branched alkylene having 1 to 8 carbon atoms, and when D is branched alkylene, the carbon atom in the branched chain is optionally bonded further to Ar to form 4- to 8-membered ring, Ar is optionally substituted aromatic ring, optionally substituted aromatic heterocycle or fused aromatic heterocycle having at least one atom selected from oxygen atom, nitrogen atom and sulfur atom as a heteroatom, and wherein the optional substituents are selected from the group consisting of (a) halogen, (b) alkyl having 1 to 6 carbon atoms, (c) alkoxy having 1 to 6 carbon atoms, (d) haloalkyl having 1 to 6 carbon atoms, (e) hydroxy, (f) amino, (g) dialkylamino, wherein the two alkyl are the same or different alkyl having 1 to 6 carbon atoms, (h) nitro, (i) cyano, and (j) amidino optionally substituted by one or more alkyl having 1 to 6 carbon atoms, provided that when X is NH—C=O, SO or $SO_2$, $R^2$ is hydrogen, alkyl, optionally substituted arylalkyl, optionally substituted aromatic ring or optionally substituted aromatic heterocycle having at least one atom selected from oxygen atom, nitrogen atom and sulfur atom as a heteroatom, when $R^1$ is a group of the formula (5) to formula (7), X is C=O or C=S and $R^2$ is hydrogen or alkyl, and when $R^1$ is a group of the formula (5), D is optionally substituted linear or branched alkylene having 2 to 8 carbon atoms, and when D is branched alkylene, the carbon atom in the branched chain is optionally bonded further to Ar to form 4- to 8-membered ring, or an optically active compound thereof or a pharmaceutically acceptable salt thereof.

2. The pyrrolidine compound of claim 1, wherein, in the formula (I), $R^1$ is a group of the formula (1), (3), (6), or (7), an optically active compound thereof or a pharmaceutically acceptable salt thereof.

3. The pyrrolidine compound of claim 1, wherein, in the formula (I), X is C=O, NH—C=O, SO or $SO_2$, an optically active compound thereof or a pharmaceutically acceptable salt thereof.

4. The pyrrolidine compound of claim 1, wherein, in the formula (I), $R^1$ is a group of the formula (1), X is C=O, $R^2$ is hydrogen, D is ethylene or trimethylene, Ar is optionally substituted aromatic ring or an optionally substituted aromatic heterocycle or fused aromatic heterocycle having at least one atom selected from oxygen atom, nitrogen atom and sulfur atom as a heteroatom, $R^3$ and $R^4$ are the same or different and each is hydrogen or alkyl, or $R^3$ and $R^4$ in combination form carbonyl, p, q, r, s, t and u are 1, and Z is carbon atom, an optically active compound thereof or a pharmaceutically acceptable salt thereof.

5. The pyrrolidine compound of claim 1, which is selected from (S)-N-(1-(2-phenylethyl)pyrrolidin-3-yl)-1-adamantanecarboxamide, (S)-N-(1-(2-(4-fluorophenyl)ethyl)pyrrolidin-3-yl)-1-adamantanecarboxamide, (S)-N-(1-(2-(3-fluorophenyl)ethyl)pyrrolidin-3-yl)-1-adamantanecarboxamide, (S)-N-(1-(2-(2-fluorophenyl)ethyl)pyrrolidin-3-yl)-1-adamantanecarboxamide, (S)-N-(1-(3-phenylpropyl)pyrrolidin-3-yl)-1-adamantanecarboxamide, (S)-N-(1-(3-(4-fluorophenyl)propyl)pyrrolidin-3-yl)-1-adamantanecarboxamide, (S)-N-(1-(2-phenylethyl)pyrrolidin-3-yl) dicyclohexylacetamide, (S)-N-(1-(2-(4-fluorophenyl)ethyl)pyrrolidin-3-yl) dicyclohexylacetamide, (S)-N-(1-(2-(4-fluorophenyl)ethyl)pyrrolidin-3-yl)-10,11-dihydrodibenzo[a,d]cycloheptene-5-carboxamide, (S)-1,1-dicyclohexyl-3-(1-(2-(4-fluorophenyl)ethyl) pyrrolidin-3-yl)urea, N-methyl-N-(1-(2-(4-fluorophenyl)ethyl)pyrrolidin-3-yl)-1-adamantanecarboxamide, and (S)-N-(1-(2-(4-fluorophenyl)ethyl)pyrrolidin-3-yl)-(4-azatricyclo[4.3.1.1(3,8)]undecan-4-yl)carboxamide or a pharmaceutically acceptable salt thereof.

6. A pharmaceutical composition comprising the pyrrolidine compound of claim 1, an optically active compound thereof or a pharmaceutically acceptable salt thereof, and a pharmaceutically acceptable additive.

7. A method for antagonizing a 5-$HT_2$ receptor in a patient, which comprises administering to a patient in need thereof a therapeutically effective amount of the pyrrolidine compound of claim 1, an optically active compound thereof or a pharmaceutically acceptable salt thereof.

8. A method for suppressing platelet aggregation in a patient, which comprises administering to a patient in need thereof a therapeutically effective amount of the pyrrolidine compound of claim 1, an optically active compound thereof or a pharmaceutically acceptable salt thereof.

9. A method for promoting lacrimation in a patient, which comprises administering to a patient in need thereof a therapeutically effective amount of the pyrrolidine compound of claim 1, an optically active compound thereof or a pharmaceutically acceptable salt thereof.

10. A method for treatment of arterial obstruction in a patient, which comprises administering to a patient in need thereof a therapeutically effective amount of the pyrrolidine compound of claim 1, an optically active compound thereof or a pharmaceutically acceptable salt thereof.

11. A method for treatment of thrombosis in a patient, which comprises administering to a patient in need thereof a therapeutically effective amount of the pyrrolidine compound of claim 1, an optically active compound thereof or a pharmaceutically acceptable salt thereof.

12. A method for ameliorating a peripheral circulation disorder in a patient, which comprises administering to a patient in need thereof a therapeutically effective amount of the pyrrolidine compound of claim 1, an optically active compound thereof or a pharmaceutically acceptable salt thereof.

* * * * *